United States Patent
Tsubusaki et al.

(10) Patent No.: US 10,377,837 B2
(45) Date of Patent: Aug. 13, 2019

(54) ANTIBODY-DRUG CONJUGATE HAVING CYCLIC BENZYLIDENE ACETAL LINKER

(71) Applicant: NOF CORPORATION, Tokyo (JP)

(72) Inventors: Takuma Tsubusaki, Kawasaki (JP); Yuji Yamamoto, Kawasaki (JP)

(73) Assignee: NOF CORPORATION, Tokyo (JP)

( * ) Notice: Subject to any disclaimer, the term of this patent is extended or adjusted under 35 U.S.C. 154(b) by 0 days.

(21) Appl. No.: 15/512,727

(22) PCT Filed: Oct. 22, 2015

(86) PCT No.: PCT/JP2015/079871
§ 371 (c)(1),
(2) Date: Mar. 20, 2017

(87) PCT Pub. No.: WO2016/063959
PCT Pub. Date: Apr. 28, 2016

(65) Prior Publication Data
US 2017/0290919 A1    Oct. 12, 2017

(30) Foreign Application Priority Data

Oct. 24, 2014 (JP) .................................. 2014-217466

(51) Int. Cl.
| | |
|---|---|
| *C08F 8/12* | (2006.01) |
| *A61K 39/395* | (2006.01) |
| *A61K 45/00* | (2006.01) |
| *A61K 47/22* | (2006.01) |
| *C07K 16/00* | (2006.01) |
| *C07C 45/36* | (2006.01) |
| *C07K 16/18* | (2006.01) |
| *C07K 19/00* | (2006.01) |
| *A61K 47/50* | (2017.01) |

(Continued)

(52) U.S. Cl.
CPC .............. *C08F 8/12* (2013.01); *A61K 39/395* (2013.01); *A61K 45/00* (2013.01); *A61K 47/22* (2013.01); *A61K 47/50* (2017.08); *C07C 45/36* (2013.01); *C07K 16/00* (2013.01); *C07K 16/18* (2013.01); *C07K 19/00* (2013.01); *C07D 317/28* (2013.01); *C07D 405/06* (2013.01); *C07D 405/14* (2013.01); *C07K 2317/24* (2013.01); *C07K 2317/30* (2013.01); *C07K 2317/50* (2013.01); *C07K 2317/90* (2013.01); *C07K 2317/92* (2013.01)

(58) Field of Classification Search
CPC ...... A61K 47/48; A61K 47/50; A61K 39/395; A61K 45/00; A61K 47/22; C07C 45/36; C07K 19/00; C07K 16/18; C07K 2317/90; C07K 2317/92; C07K 2317/50; C07K 2317/24; C07K 2317/30; C07K 16/00; C08F 8/12; C07D 405/06; C07D 317/28; C07D 405/14
See application file for complete search history.

(56) References Cited

U.S. PATENT DOCUMENTS

| | | | |
|---|---|---|---|
| 5,773,001 | A | 6/1998 | Hamann et al. |
| 2016/0046763 | A1 | 2/2016 | Tsubusaki et al. |

FOREIGN PATENT DOCUMENTS

| | | |
|---|---|---|
| EP | 3130587 A1 | 2/2017 |
| EP | 3 279 236 A1 | 2/2018 |

(Continued)

OTHER PUBLICATIONS

Malhotra, R., "High-molecular-weight polyethylene glycol protects cardiac myocytes from hypoxia-and reoxygenation-induced cell death and preserves ventricular function." American Journal of Physiology-Heart and Circulatory Physiology 300.5 (2011): H1733-H1742.*

(Continued)

*Primary Examiner* — John M Mauro
(74) *Attorney, Agent, or Firm* — Sughrue Mion, PLLC

(57) ABSTRACT

An antibody-drug conjugate having a cyclic benzylidene acetal linker represented by formula (1) or formula (2), wherein Y is an antibody; D is a drug; $R^1$ and $R^6$ are each independently a hydrogen atom or a hydrocarbon group; $R^2$, $R^3$, $R^4$ and $R^5$ are each independently an electron-withdrawing or electron-donating substituent or a hydrogen atom; s is 1 or 2, t is 0 or 1, and s+t is 1 or 2; w is an integer of 1 to 20; and $Z^1$ and $Z^2$ are each independently a selected divalent spacer:

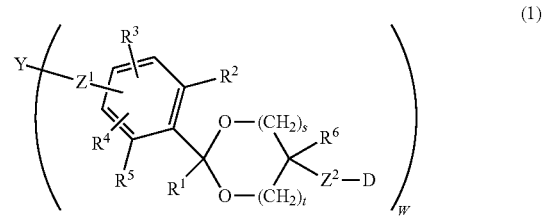

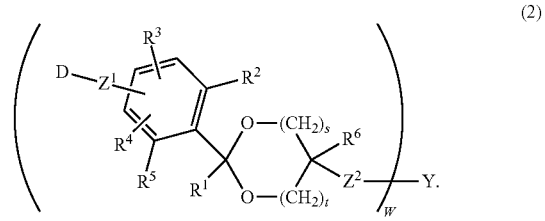

11 Claims, 2 Drawing Sheets

(51) Int. Cl.
    *C07D 405/14*    (2006.01)
    *C07D 317/28*    (2006.01)
    *C07D 405/06*    (2006.01)

(56) References Cited

FOREIGN PATENT DOCUMENTS

| WO | 2007/131193 A2 | 11/2007 |
|---|---|---|
| WO | 2011/012715 A1 | 2/2011 |
| WO | 2013/173337 A2 | 11/2013 |
| WO | 2014/157150 A1 | 10/2014 |
| WO | 2015/152182 A1 | 10/2015 |

OTHER PUBLICATIONS

Huang, et al., "pH-labile sheddable block copolymers by RAFT polymerization: Synthesis and potential use as siRNA conjugates", European Polymer Journal, 2013, vol. 49, Issue No. 10, 12 pages total.

Perez, et al., "Antibody-drug conjugates: current status and future directions", Drug Discovery Today, vol. 19, Issue No. 7, Jul. 2014, pp. 869-881.

Abu-Aid, et al., "Kinetics and Mechanism of the Hydrolysis of Benzylidene Benzoylhydrazone Derivatives", An-Najah University Journal for Research, vol. 1, Issue No. 6, 1989, pp. 23-33.

Cardillo, et al., "Humanized Anti-Trop-2 IgG-SN-38 Conjugate for Effective Treatment of Diverse Epithelial Cancers: Preclinical Studies in Human Cancer Xenograft Models and Monkeys", Clinical Cancer Research vol. 17, Issue No. 10, May 15, 2011; pp. 3157-3169.

Finniss, et al., "A versatile acid-labile linker for antibody-drug conjugates", Med. Chem Comm., vol. 5, 2014, 4 pages total.

Search Report dated Dec. 15, 2015, issued by the International Searching Authority in counterpart International Patent Application No. PCT/JP2015/079871 (PCT/ISA/210).

Siyeon Lee et al., "Cyclic acetals as cleavable linkers for affinity capture", Organic & Biomolecular Chemistry, vol. 13, No. 31, XP055363605, Jan. 1, 2015, pp. 8445-8452.

Communication dated Jun. 6, 2018, issued by the European Patent Office in counterpart European application No. 15851936.3.

* cited by examiner

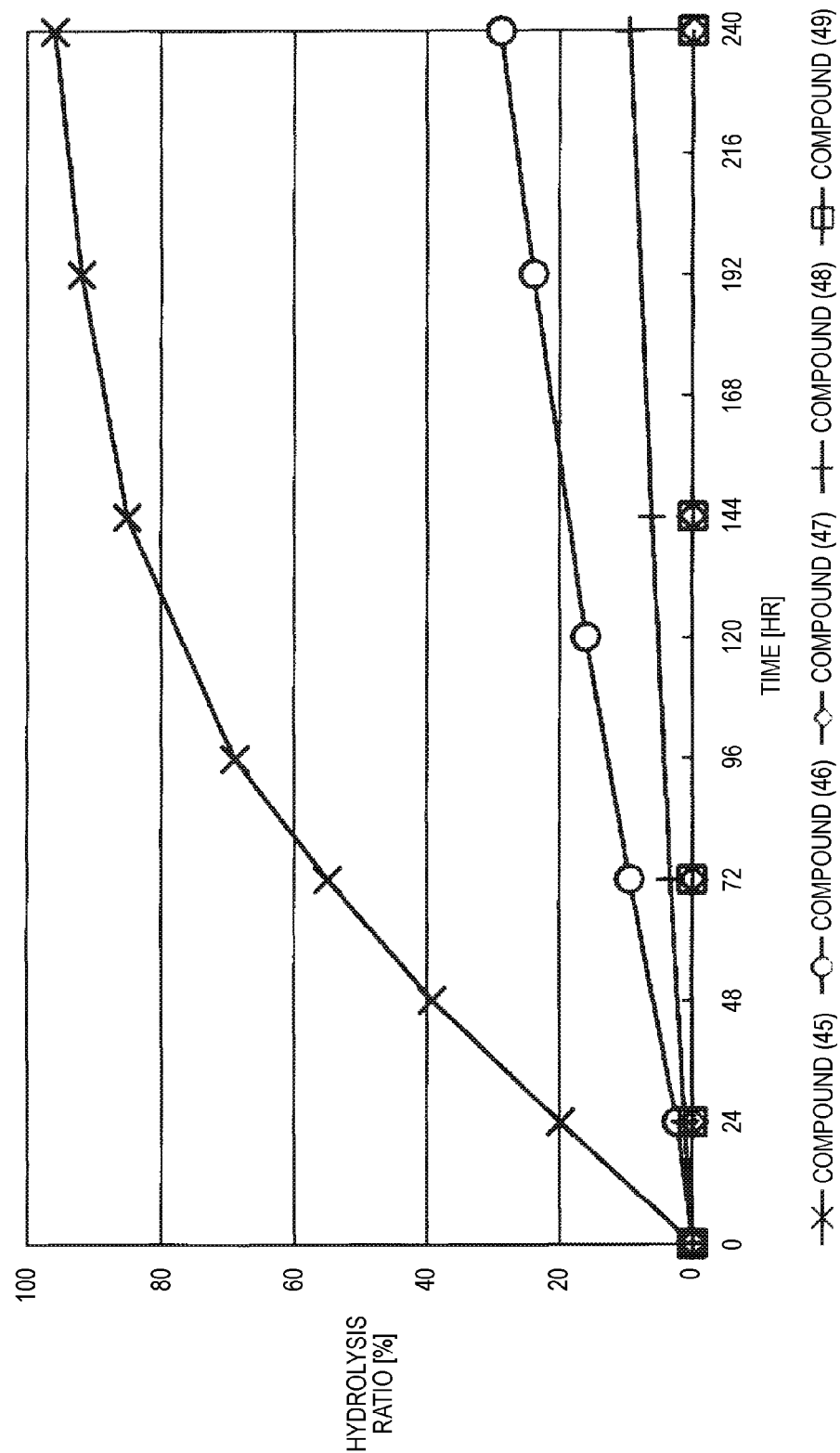

ANTIBODY-DRUG CONJUGATE HAVING CYCLIC BENZYLIDENE ACETAL LINKER

TECHNICAL FIELD

The present invention relates to an antibody-drug conjugate having an acid hydrolyzable linker which is hydrolyzable in an acidic environment in the living body.

BACKGROUND ART

An antibody-drug conjugate (ADC) is an antibody drug in which an antibody is bound to a drug and which aims to efficiently deliver the drug to a disease site by utilizing the antigen specificity of the antibody, and in recent years, it is one of the most rapidly growing techniques in the field of cancer treatment. The ADC is composed of each part of an antibody, a drug and a linker for binding between the antibody and the drug.

The linker plays a role to stably bind the antibody and the drug until the ADC reaches the target site, and on the other hand, the linker is required to have a function in many cases that it is selectively cleaved at the target site to detach the drug from the antibody. As such cleavable linkers, an acid hydrolyzable linker which is cleaved in a low pH environment in the cell, a disulfide linker which is cleaved in a reductive environment in the cell, a dipeptide linker which is cleaved by increased expression of enzymes in the cancer cell and the like have been developed.

Hitherto, as the acid hydrolyzable linker in the field of ADC, a hydrazone linker is mainly used. Including Mylotarg (registered trademark) which has received at first the FDA approval as the ADC, the hydrazone linkers are introduced into ADCs currently in clinical trial stage.

However, it is reported that the hydrazone linker is hydrolyzed during blood circulation and the drug is released in sites other than the target site, and as a result, there is a possibility of causing side effects, for example, systemic toxicity or organ specific toxicity. It is believed that this is caused by instability of the hydrazone in pH of the blood (Non-Patent Document 1).

In Patent Document 1, it is described that the hydrolysis rate of hydrazone can be regulated by changing substituents on the benzene ring in the vicinity of the hydrazone, and antibody-drug conjugates having several kinds of hydrazone linkers having different substituents on the benzene ring are disclosed. However, evaluation data of the hydrolysis rate are not shown.

Moreover, in Non-Patent Document 2, kinetics study of the hydrolysis of hydrazone is described and it is shown that in the hydrolysis of hydrazone, the influence of differences in the substituents present on the neighboring benzene ring on the hydrolysis rate is small. Therefore, there is a possibility that the hydrazone is not the best choice for the purpose of regulating the hydrolysis rate.

As other acid hydrolyzable linkers used for ADC, an ester linker (Non-Patent Document 3) and a silyl ether linker (Non-Patent Document 4) are reported, but these are not linkers which are able to regulate the hydrolysis rate to match a variety of pH values.

As described above, there has been no example relating to an acid hydrolyzable linker in which the hydrolysis rate is able to be accurately controlled in accordance with the pH of the target site in the living body.

PRIOR ART DOCUMENT

Patent Document

Patent Document 1: U.S. Pat. No. 5,773,001

Non-Patent Document

Non-Patent Document 1: Drug Discovery Today 2014, 19 (7), 869-881
Non-Patent Document 2: An-Najah J. Res. 1989, Vol. 1, No. 6, 23-33
Non-Patent Document 3: Clin. Cancer Res. 2011, 17, 3157-3169
Non-Patent Document 4: Med. Chem. Commun. 2014, 5, 1355-1358

SUMMARY OF THE INVENTION

Problems that the Invention is to Solve

The deviation of pH at each portion of the living body is very small, and the acid hydrolyzable linker of the antibody-drug conjugate is required to be properly hydrolyzed in response to a slight difference in pH between the target site and the blood. For example, while the periphery of a tumor tissue is an acidic environment in comparison with pH of a normal tissue, it is weakly acidic pH of approximately 6.0. Moreover, an endosome interior is also weakly acidic pH of 5.5 to 6.0 and is gradually acidified to approach pH of 4.5 to 5.0 which is the pH of a lysosome. Since the endosome is finally fused with the lysosome, it is necessary that the drug is detached from the antibody-drug conjugate at around pH 5.5 to escape from the endosome, in order to avoid decomposition or denaturation of the drug taken up in the endosome by a lysosomal enzyme. Thus, in order to selectively detach the drug at the target site, the hydrolysis rate of the linker at the pH of the weakly acidic environment in the living body must be accurately controlled.

An object of the invention is to provide an antibody-drug conjugate having a linker which is able to accurately control a hydrolysis rate at the pH of the weakly acidic environment in the living body.

Means for Solving the Problems

As a result of the intensive investigations to solve the problems described above, the inventors have developed an antibody-drug conjugate having a cyclic benzylidene acetal linker which is able to accurately control a hydrolysis rate at the pH of the weakly acidic environment in the living body.

The feature of the invention resides in that a drug is bound to an antibody through a cyclic benzylidene acetal linker having substituent(s). By properly selecting the kind and the position of the substituent(s) on the benzene ring of the cyclic benzylidene acetal linker, the electron density and the degree of steric hindrance around the acetal group which affect the hydrolysis rate of the acetal linker can be regulated. Based on the feature, it is possible to impart the desired hydrolysis rate to the acetal linker and it becomes possible to detach the drug at an arbitrary rate from the antibody which is bound to the drug through the cyclic benzylidene acetal linker.

The antibody-drug conjugate of the invention can be synthesized by linking an antibody which is bound to a cyclic benzylidene acetal linker compound having substituent(s) to a drug, or by linking a drug which is bound to the linker compound to an antibody.

Thus, the invention is as follows.

[1]

An Antibody-drug conjugate having a cyclic benzylidene acetal linker represented by formula (1) or formula (2):

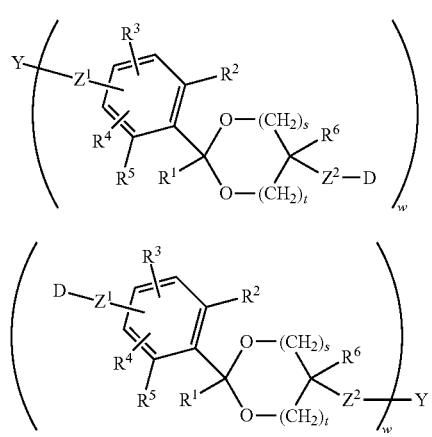

in formula (1) and formula (2), Y is an antibody; D is a drug; $R^1$ and $R^6$ are each independently a hydrogen atom or a hydrocarbon group; $R^2$, $R^3$, $R^4$ and $R^5$ are each independently an electron-withdrawing or electron-donating substituent or a hydrogen atom; s is 1 or 2, t is 0 or 1, and s+t is 1 or 2; w is an integer of 1 to 20; and $Z^1$ and $Z^2$ are each independently a selected divalent spacer.

[2]

The antibody-drug conjugate of [1], wherein s is 1 and t is 0, $R^2$ and $R^5$ are each a hydrogen atom, and a sum ($\Sigma\sigma$) of substituent constants ($\sigma$) in $R^3$, $R^4$ and Y—$Z^1$ in formula (1) or in $R^3$, $R^4$ and D-$Z^1$ in formula (2) satisfies $-0.30 \leq \Sigma\sigma \leq 1.05$.

[3]

The antibody-drug conjugate of [1], wherein s is 1 and t is 0, at least one of $R^2$ and $R^5$ is the substituent, and a sum ($\Sigma\sigma$) of substituent constants ($\sigma$) in $R^3$, $R^4$ and Y—$Z^1$ in formula (1) or in $R^3$, $R^4$ and D-$Z^1$ in formula (2) satisfies $-1.71 \leq \Sigma\sigma \leq 0.88$.

[4]

The antibody-drug conjugate of [1], wherein s is 1 and t is 1, or s is 2 and t is 0, $R^2$ and $R^5$ are each a hydrogen atom, and a sum ($\Sigma\sigma$) of substituent constants ($\sigma$) in $R^3$, $R^4$ and Y—$Z^1$ in formula (1) or in $R^3$, $R^4$ and D-$Z^1$ in formula (2) satisfies $-0.19 \leq \Sigma\sigma \leq 0.57$.

[5]

The antibody-drug conjugate of [1], wherein s is 1 and t is 1, or s is 2 and t is 0, at least one of $R^2$ and $R^5$ is the substituent, and a sum ($\Sigma\sigma$) of substituent constants ($\sigma$) in $R^3$, $R^4$ and Y—$Z^1$ in formula (1) or in $R^3$, $R^4$ and D-$Z^1$ in formula (2) satisfies $-0.98 \leq \Sigma\sigma \leq 0.48$.

[6]

The antibody-drug conjugate of any one of [1] to [5], wherein the antibody is a monoclonal antibody, a single chain monoclonal antibody, a bispecific antibody or a monoclonal antibody fragment that binds to a target cell.

[7]

The antibody-drug conjugate of any one of [1] to [5], wherein the antibody is a resurfaced monoclonal antibody, a resurfaced single chain monoclonal antibody or a resurfaced monoclonal antibody fragment that binds to a target cell.

[8]

The antibody-drug conjugate of any one of [1] to [5], wherein the antibody is a human monoclonal antibody, a humanized monoclonal antibody, a humanized single chain monoclonal antibody or a humanized monoclonal antibody fragment that binds to a target cell.

[9]

The antibody-drug conjugate of [6], wherein the antibody is a chimeric antibody, a chimeric antibody fragment, a domain antibody or a domain antibody fragment.

[10]

The antibody-drug conjugate of any one of [1] to [5], wherein the drug is a chemotherapeutic drug.

[11]

The antibody-drug conjugate as claimed in any one of [1] to [10], wherein $Z^1$ and $Z^2$ are each independently an ether bond, an ester bond, a carbonate bond, a urethane bond, an amide bond, a thioether bond, a disulfide bond, a 1H-1,2,3-triazole-1,4-diyl group, a secondary amino group, an aliphatic hydrocarbon group containing any of these bonds and groups, a single bond or an aliphatic hydrocarbon group, but in the case where at least one of $Z^1$ and $Z^2$ is an ether bond, an ester bond, a carbonate bond, a urethane bond, an amide bond, a thioether bond, a disulfide bond, a 1H-1,2,3-triazole-1,4-diyl group, a secondary amino group or an aliphatic hydrocarbon group containing any of these bonds and groups and a plurality of identical structural units are bound, a number of the structural units described above is 2 or less.

[12]

A compound having a cyclic benzylidene acetal linker represented by formula (3) or formula (4):

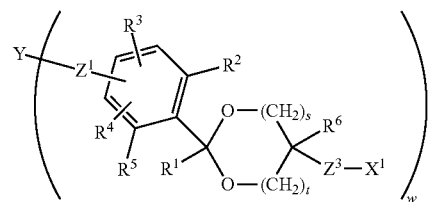

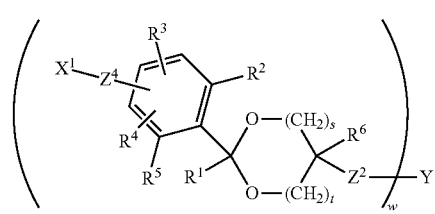

in formula (3) and formula (4), Y is an antibody; $R^1$ and $R^6$ are each independently a hydrogen atom or a hydrocarbon group; $R^2$, $R^3$, $R^4$ and $R^5$ are each independently an electron-withdrawing or electron-donating substituent or a hydrogen atom; $X^1$ is a reactive functional group capable of linking to a drug by a covalent bond; s is 1 or 2, t is 0 or 1, and s+t is 1 or 2; w is an integer of 1 to 20; and $Z^1$, $Z^2$, $Z^3$ and $Z^4$ are each independently a selected divalent spacer.

[13]

The compound of [12], wherein $X^1$ is selected from the group consisting of an active ester group, an active carbonate group, an aldehyde group, an isocyanate group, an isothiocyanate group, an epoxy group, a maleimide group, a vinyl sulfone group, an acryl group, a sulfonyloxy group, a carboxyl group, a thiol group, a dithiopyridyl group, an α-haloacetyl group, an alkynyl group, an allyl group, a vinyl group, an amino group, an oxyamino group, a hydrazide group, an azide group and a hydroxyl group.

[14]

The compound of [12] or [13], wherein $X^1$ is selected from the group consisting of formula (a), formula (b), formula (c), formula (d), formula (e), formula (f), formula (g), formula (h), formula (i), formula (j), formula (k), formula (l), formula (m), formula (n), formula (o), formula (p) and formula (q):

(a)

(b)

(c)

(d)

(e)

(f) —COOH (g) —SH (h)

(i)

(j) —C≡C—R$^{11}$ (k) —NH$_2$ (l) —O—NH$_2$ (m)

(n) —N$_3$ (o) —OH (p)

(q)

wherein $R^7$ is a hydrogen atom or a sulfo group; $R^8$ and $R^{11}$ are each independently a hydrogen atom or a hydrocarbon group having from 1 to 5 carbon atoms; $R^9$ is a hydrocarbon group having from 1 to 10 carbon atoms which may contain a halogen atom; and $R^{10}$ is a halogen atom selected from the group consisting of a chlorine atom, a bromine atom and an iodine atom.

[15]

A compound having a cyclic benzylidene acetal linker represented by formula (5) or formula (6):

(5)

(6)

in formula (5) and formula (6), D is a drug; $R^1$ and $R^6$ are each independently a hydrogen atom or a hydrocarbon group; $R^2$, $R^3$, $R^4$ and $R^5$ are each independently an electron-withdrawing or electron-donating substituent or a hydrogen atom; $X^2$ is a reactive functional group capable of linking to an antibody by a covalent bond; s is 1 or 2, t is 0 or 1, and s+t is 1 or 2; and $Z^1$, $Z^2$, $Z^3$ and $Z^4$ are each independently a selected divalent spacer.

[16]

The compound of [15], wherein $X^2$ is selected from the group consisting of an active ester group, an active carbonate group, an aldehyde group, an isocyanate group, an isothiocyanate group, an epoxy group, a maleimide group, a vinyl sulfone group, an acryl group, a sulfonyloxy group, a carboxy group, a thiol group, a dithiopyridyl group, an α-haloacetyl group, an alkynyl group, an allyl group, a vinyl group, an amino group, an oxyamino group, a hydrazide group, an azide group and a hydroxyl group.

[17]

The compound of [15] or [16], wherein $X^2$ is selected from the group consisting of formula (a), formula (b), formula (c), formula (d), formula (e), formula (f), formula (g), formula (h), formula (i), formula (j), formula (k), formula (l), formula (m), formula (n), formula (o), formula (p) and formula (q):

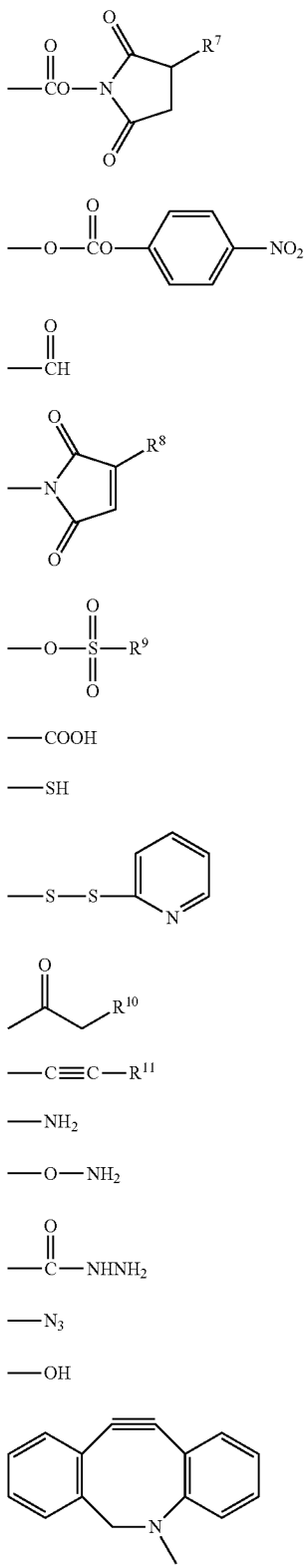

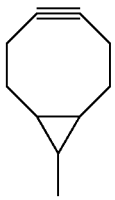

wherein $R^7$ is a hydrogen atom or a sulfo group; $R^8$ and $R^{11}$ are each independently a hydrogen atom or a hydrocarbon group having from 1 to 5 carbon atoms; $R^9$ is a hydrocarbon group having from 1 to 10 carbon atoms which may contain a halogen atom; and $R^{10}$ is a halogen atom selected from the group consisting of a chlorine atom, a bromine atom and an iodine atom.

[18]

The compound of any one of [12] to [17], wherein $Z^3$ and $Z^4$ are each independently an ether bond, an ester bond, a carbonate bond, a urethane bond, an amide bond, a thioether bond, a disulfide bond, a 1H-1,2,3-triazole-1,4-diyl group, a secondary amino group, an aliphatic hydrocarbon group containing any of these bonds and groups, a single bond or an aliphatic hydrocarbon group, but in the case where at least one of $Z^3$ and $Z^4$ is an ether bond, an ester bond, a carbonate bond, a urethane bond, an amide bond, a thioether bond, a disulfide bond, a 1H-1,2,3-triazole-1,4-diyl group, a secondary amino group or an aliphatic hydrocarbon group containing any of these bonds and groups and a plurality of identical structural units are bound, a number of the structural units described above is 2 or less.

Advantage of the Invention

In the antibody-drug conjugate having a cyclic benzylidene acetal linker according to the invention, the hydrolysis rate of the cyclic benzylidene acetal linker is able to be accurately controlled in accordance with the pH of a weakly acidic environment in the living body. Therefore, it is possible to detach the drug at the desired rate from the antibody-drug conjugate at the pH of the living body site which is the target of the antibody-drug conjugate.

BRIEF DESCRIPTION OF THE DRAWINGS

FIG. 2 shows results of the hydrolysis test in HEPES deuterated water buffer at pD 7.4 at 37° C. using the compounds of formula (45), formula (46), formula (47), formula (48) and formula (49) described in Examples.

MODE FOR CARRYING OUT THE INVENTION

Figure 1:
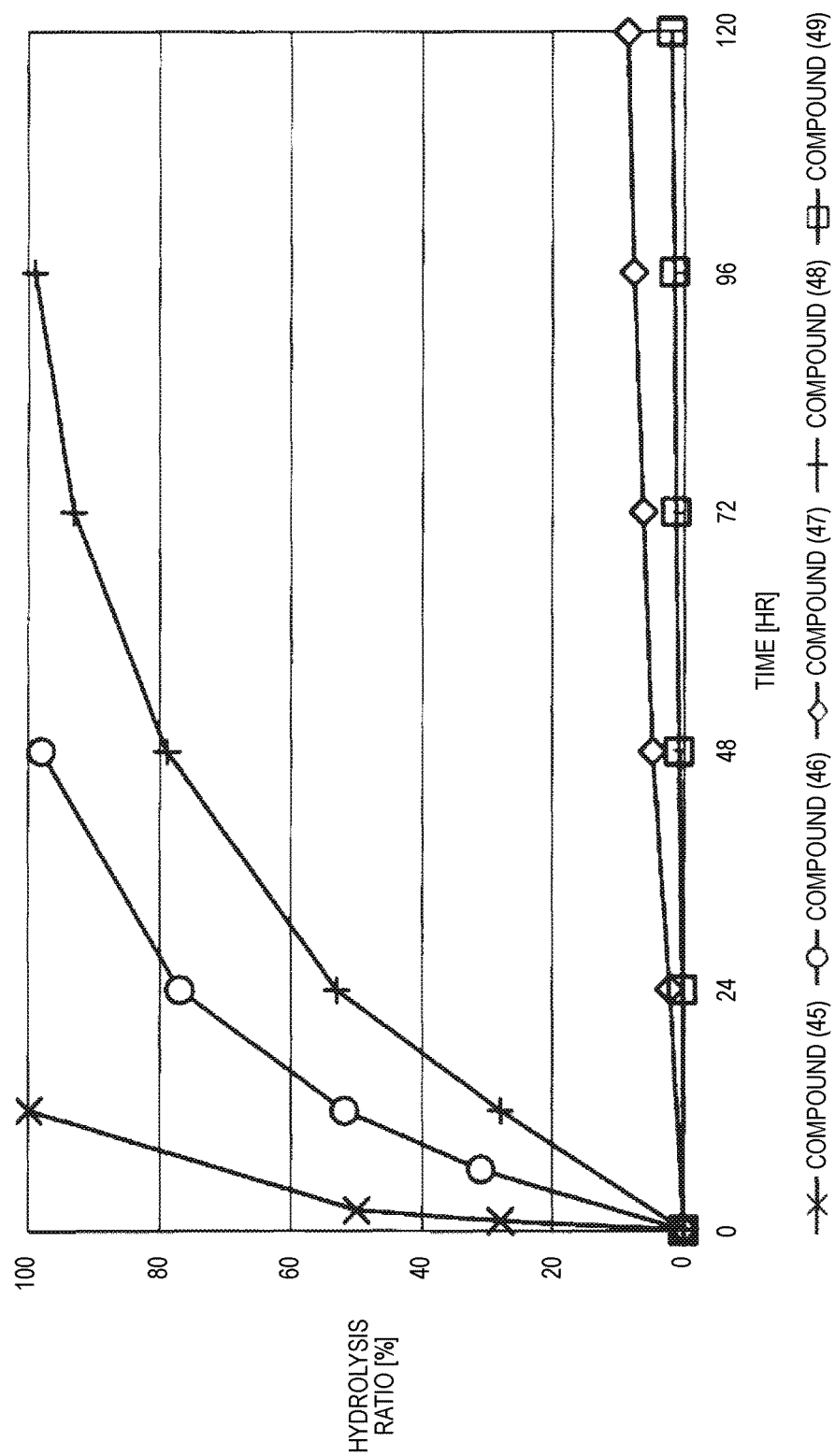
FIG. 1 shows results of the hydrolysis test in MES deuterated water buffer at pD 5.5 at 37° C. using the compounds of formula (45), formula (46), formula (47), formula (48) and formula (49) described in Examples.

The invention will be described in detail hereinafter.

The term "acetal" as used in the specification means both of an acetal structure derived from an aldehyde and an acetal structure derived from a ketone, that is, a ketal structure.

The term "cyclic acetal" as used in the invention means both of a 1,3-dioxolane structure of a 5-membered ring which is s is 1 and t is 0 in formula (1) or formula (2) and a 1,3-dioxane structure of a 6-membered ring which is s is 1 and t is 1 or s is 2 and t is 0 in formula (1) or formula (2).

Each of $R^1$ and $R^6$ in formula (1) or formula (2) of the invention is a hydrogen atom or a hydrocarbon group, a number of carbon atoms of the hydrocarbon group is preferably 10 or less, and specific examples of the hydrocarbon group include a methyl group, an ethyl group, a propyl group, an isopropyl group, a tert-butyl group, a phenyl group and a benzyl group. A preferred embodiment of $R^1$ is a hydrogen atom or a methyl group, and a hydrogen atom is more preferred.

The benzene ring in formula (1) or formula (2) of the invention may have a plurality of substituents. By properly selecting the kind, the position and the degree of electron-donating property and electron-withdrawing property of the substituents on the benzene ring, it is possible to regulate the electron density and the degree of steric hindrance around the acetal group which affects the hydrolysis rate of the cyclic acetal linker. This makes it possible to impart a desired hydrolysis rate to the cyclic acetal linker.

In the specification, the substituent on the benzene ring in formula (1) or formula (2) is described using a "substituent constant (σ)" which means a substituent constant in the Hammett's rule which quantifies the effect of the substituent on the reaction rate or equilibrium of benzene derivative. However, as is known, the Hammett's rule is applied only to a para-substituted or meta-substituted benzene derivative and cannot be applied to an ortho-substituted benzene derivative which is affected by steric hindrance. Therefore, in the case of ortho-substituted benzene derivative, the substituent constant means the substituent constant in the Taft's equation which extends the Hammett's rule described above.

In the para-substituted or meta-substituted benzene derivative described above, the Hammett's rule is represented by equation (7) shown below.

$$\log(k/k_0) = \rho\sigma \qquad (7)$$

(in the equation above, k is a rate constant or equilibrium constant in an arbitrary reaction of para-substituted or meta-substituted benzene derivative, $k_0$ is a rate constant or equilibrium constant in the case where the benzene derivative does not have a substituent, that is, the substituent is a hydrogen atom, ρ is a reaction constant, and σ is a substituent constant.)

The reaction constant (ρ) in equation (7) described above is a constant which is determined depending on reaction conditions, for example, the kind of reaction, temperature or solvent, and can be calculated from the slope of Hammett plots. In the specification, in order to perform evaluation of hydrolyzability of the cyclic benzylidene acetal by measurement of $^1$H-NMR, polyethylene glycol which is the representative hydrophilic polymer is bound to the cyclic benzylidene acetal in place of the antibody, thereby performing the hydrolysis test. In the case where the cyclic benzylidene acetal has a 1,3-dioxolane structure, the constant is calculated as "ρ=−2.7" from the results of the hydrolysis tests performed for the compounds of formula (45), formula (46) and formula (47). Also, in the case where it has a 1,3-dioxane structure, the constant is calculated as "ρ=−4.8" from the results of the hydrolysis tests performed for the compounds of formula (48) and formula (49).

The substituent constant (σ) in equation (7) described above is a constant which is determined only depending on the kind and position of the substituent, regardless of the kind of reaction. In the case where no substituent is present, that is, the substituent is a hydrogen atom, the constant is "0". The term "electron-withdrawing" as used in the specification means the case where σ is a positive value and the term "electron-donating" means the case where σ is a negative value.

As described above, the Hammett's rule is applied only to para-substituted or meta-substituted benzene derivative and cannot be applied to the case of ortho-substituted benzene derivative which is affected by steric hindrance. Therefore, it is the Taft's equation that the effect of such steric hindrance is introduced as a factor of the position, that is, a position constant (Es) of the substituent, to extend the Hammett's rule so that it can also be applied to the case of the ortho-substituted benzene derivative. The Taft's equation is represented by equation (8) shown below.

$$\log(k/k_0) = \rho^*\sigma^* + Es \qquad (8)$$

(in the equation above, k is a rate constant or equilibrium constant in an arbitrary reaction of para-substituted or meta-substituted benzene derivative, $k_0$ is a rate constant or equilibrium constant in the case where the benzene derivative does not have a substituent, that is, the substituent is a hydrogen atom, $\rho^*$ is a reaction constant, $\sigma^*$ is a substituent constant, and Es is a position constant of the substituent.)

As is known, since the reaction constant (ρ) of para-substituted or meta-substituted benzene derivative and the reaction constant ($\rho^*$) of ortho-substituted benzene derivative are approximately equal, it is defined in the specification that ρ and $\rho^*$ are the same. Since the substituent constant ($\sigma^*$) in the ortho position is similar to the substituent constant in the para position as described, for example, in "Charton, M. Can. J. Chem. 1960, 38, 2493-2499", to the substituent constant in the ortho position in the specification is applied a corresponding substituent constant in the para position.

The substituent constant (σ) in the para position or the meta position is described in "Hansch, C.; Leo, A.; Taft, R. W. Chem. Rev. 1991, 91, 165-195", and with respect to a substituent in which the substituent constant (σ) is unknown the constant can be measured and determined by the method described in "Hammett, L. P. Chem. Rev. 1935, 17(1), 125-136". Moreover, the position constant (Es) is described in "Unger, S. H.; Hansch, C. Prog. Phys. Org. Chem. 1976, 12, 91-118". However, as to Es as used in the specification, a hydrogen atom is defined as "0".

In formula (1) or formula (2), in the case where a plurality of substituents are present on the benzene ring, it is defined that additivity is established for the substituent constant (σ) and the position constant (Es) thereof, and the sum of σ is represented by "Σσ" and the sum of Es is represented by "ΣEs".

$Z^1$ is bound to the benzene ring of the cyclic benzylidene acetal, and Y—$Z^1$, D-$Z^1$ and the polyethylene glycol binding portion (P—$Z^1$) of polyethylene glycol derivative which is used in the hydrolysis test are also substituents of the benzene ring. The substituent constants of Y—$Z^1$, D-$Z^1$ and P—$Z^1$ can be determined by separately measuring combinations of Y and $Z^1$, D and $Z^1$ and P and $Z^1$, but, since the substituent constants of Y—$Z^1$, D-$Z^1$ and P—$Z^1$ are substantially affected largely by the structure in the vicinity of the bimding portion to the benzene ring, the effect of the other portions is so small as to be ignored. Therefore, it is possible to use a known substituent constant of a structure similar to the structure in the vicinity of the binding portion to the benzene ring in place of separately measuring the substituent constants of Y—$Z^1$, D-$Z^1$ and P—$Z^1$.

It is defined that each of the substituent constants of Y—$Z^1$, D-$Z^1$ and P—$Z^1$ in the specification can be substituted with a substituent constant of a structure in which atom(s) bound to the third atom counted from the atom bound to the benzene ring of the backbone atoms of the main chain of each of Y—$Z^1$, D-$Z^1$ and P—$Z^1$, excepting the second atom, are substituted with hydrogen atom(s). However, in the case where, when the atom is substituted with a hydrogen atom, a carboxyl group is formed, it is defined that the substituent constant can be substituted with a substituent constant of a structure in which the atom is substituted with a methyl group in place of a hydrogen atom.

Specific examples of the structure of the binding portion to the benzene ring in Y—$Z^1$, D-$Z^1$ and P—$Z^1$ and the structure for the substitution are shown below. In the case of (r1) shown below, wherein the binding portion to the benzene ring in Y—$Z^1$, D-$Z^1$ or P—$Z^1$ is an ether bond, a substituent constant of (r2) shown below is applied. In the cases of (r3) and (r5) shown below, wherein the binding portion to the benzene ring in Y—$Z^1$, D-$Z^1$ or P—$Z^1$ is an amide bond, substituent constants of (r4) and (r6) shown below are applied, respectively. In the case of (r7) shown below, wherein the binding portion to the benzene ring in Y—$Z^1$, D-$Z^1$ or P—$Z^1$ is a urethane bond, a substituent constant of (r8) shown below is applied.

When the equation is modified, $\log(k'/k)=\log[(k'/k_0)/(k/k_0)]=-0.30$ $\log(k'/k_0)-\log(k/k_0)=-0.30$ When equation (9) above is substituted, $\log(k'/k_0)-(-0.27)=-0.30$ $\log(k'/k_0)=-0.57$ (10)

Here, when the sum ($\Sigma\sigma$) of the substituent constants is calculated using equation (10) and equation (7) above, equation (11) shown below is obtained.

$\log(k'/k_0)=-2.7\times\Sigma\sigma=-0.57$ $\Sigma\sigma=0.21$ (11)

Similarly, in the case where $R^2$ and $R^5$ in formula (1) or formula (2) are hydrogen atoms, when $\log(k''/k_0)$ is calcu-

| Structure of Binding Portion to Benzene Ring | | Structure for Substitution | |
|---|---|---|---|
| (r1) | 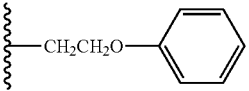 | (r2) | 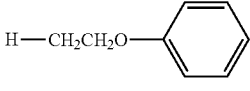 |
| (r3) | 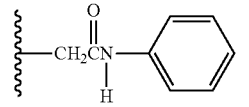 | (r4) | 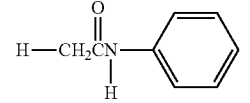 |
| (r5) | 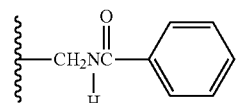 | (r6) | 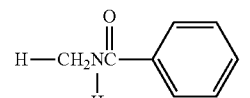 |
| (r7) | 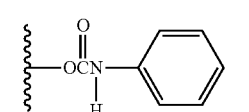 | (r8) | 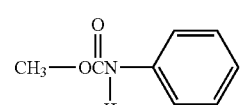 |

As to a suitable hydrolysis rate of the antibody-drug conjugate having a cyclic benzylidene acetal linker of the invention, hydrolysis half-life ($t_{1/2}$) in a buffer at pH 5.5 and 37° C. is preferably in the range from 1 hour to 6 months, more preferably in the range from 1 hour to 1 month, and still more preferably in the range from 1 hour to 24 hours. In the specification, using a numerical value derived from the compound of formula (46) described in Examples in which $t_{1/2}$ under the hydrolysis conditions described above is 12 hours, a suitable range of the sum ($\Sigma\sigma$) of substituent constants in the case where a 1,3-dioxolane structure is included is defined. When $\log(k/k_0)$ for the compound of formula (46) is calculated using equation (7) above, equation (9) shown below is obtained. However, as defined above, P—$Z^1$ in the compound of formula (46) is substituted with an ethoxy group ($CH_3CH_2O$—).

$\log(k/k_0)=-2.7\times(0.34-0.24)=-0.27$ (9)

In the case where $R^2$ and $R^5$ in formula (1) or formula (2) are hydrogen atoms, when $\log(k'/k_0)$ is calculated by taking the rate constant at the time when $t_{1/2}$ is 24 hours as k' using equation (9) and equation (7) above, equation (10) shown below is obtained.

$\log(k'/k)=\log\{(12/24)k/k\}=-0.30$ lated by taking the rate constant at the time when $t_{1/2}$ is 1 hour as k'', equation (12) shown below is obtained.

$\log(k''/k)=\log(12k/k)=1.08$

When the equation is modified, $\log(k''/k)=\log[(k''/k_0)/(k/k_0)]=1.08$ $\log(k''/k_0)-\log(k/k_0)=1.08$ When equation (9) above is substituted, $\log(k''/k_0)-(-0.27)=1.08$ $\log(k''/k_0)=0.81$ (12)

Here, when the sum ($\Sigma\sigma$) of the substituent constants is calculated using equation (12) and equation (7) above, equation (13) shown below is obtained.

$\log(k''/k_0)=-2.7\times\Sigma\sigma=0.81$ $\Sigma\sigma=-0.30$ (13)

From equation (11) and equation (13), in the case where the cyclic benzylidene acetal in formula (1) or formula (2) includes a 1,3-dioxolane structure and $R^2$ and $R^5$ are hydrogen atoms, when the range of $\Sigma\sigma$ satisfies $-0.30\leq\Sigma\sigma\leq0.21$, $t_{1/2}$ of the antibody-drug conjugate is represented by 1 hour≤$t_{1/2}$≤24 hours. Similarly, when the ranges of Σσ at 1 hour≤$t_{1/2}$≤1 month and 1 hour≤$t_{1/2}$≤6 months are calculated, −0.30≤Σσ≤0.76 at the time of 1 hour≤$t_{1/2}$≤1 month and −0.30≤Σσ≤1.05 at the time of 1 hour≤$t_{1/2}$≤6 months, respectively.

The antibody-drug conjugate of the invention can be synthesized by binding an antibody to a drug by using the cyclic benzylidene acetal linker compound. Therefore, the substituent on the benzene ring of the cyclic benzylidene acetal, which can be used in the invention, is a substituent which does not inhibit the reactions used in the synthesis process of the cyclic benzylidene acetal linker compound and the binding reaction between the antibody and the drug using the cyclic benzylidene acetal linker compound.

The substituent may be any of electron-withdrawing substituent and electron-donating substituent as far as it satisfies the conditions described above, and the substituents may be used individually or in combination. The electron-withdrawing substituent includes an acyl group having from 2 to 5 carbon atoms, an alkoxycarbonyl group having from 2 to 5 carbon atoms, a carbamoyl group having from 2 to 5 carbon atoms, an acyloxy group having from 2 to 5 carbon atoms, an acylamino group having from 2 to 5 carbon atoms, an alkoxycarbonylamino group having from 2 to 5 carbon atoms, a fluorine atom, a chlorine atom, a bromine atom, an iodine atom, an alkylsulfanyl group having from 1 to 4 carbon atoms, an alkylsulfonyl group having from 1 to 4 carbon atoms, an arylsulfonyl group having from 6 to 10 carbon atoms, a nitro group, a trifluoromethyl group and a cyano group, and preferred examples thereof include an acetyl group, a methoxycarbonyl group, a methylcarbamoyl group, an acetoxy group, an acetamide group, a methoxycarbonylamino group, a fluorine atom, a chlorine atom, a bromine atom, an iodine atom, a methylsulfanyl group, a phenylsulfonyl group, a nitro group, a trifluoromethyl group and a cyano group. The electron-donating substituent includes an alkyl group having from 1 to 4 carbon atoms, and preferred examples thereof include a methyl group, an ethyl group, a propyl group, an isopropyl group and a tert-butyl group. The substituent which is an electron-withdrawing group in the meta-position and an electron-donating group in the para- and ortho-positions includes an alkoxy group having from 1 to 4 carbon atoms, an aryl group having from 6 to 10 carbon atom and an aryloxy group having from 6 to 10 carbon atoms, and preferred examples thereof include a methoxy group, an ethoxy group, a propoxy group, an isopropoxy group, a tert-butoxy group, a phenyl group and a phenoxy group.

In the case where the cyclic benzylidene acetal in formula (1) or formula (2) includes a 1,3-dioxolane structure and at least one of $R^2$ and $R^5$ is a substituent other than a hydrogen atom, using the position constants (Es) of a phenyl group which has the largest influence of steric hindrance and a fluorine atom which has the smallest influence of steric hindrance among the substituents described above, the ranges of Σσ in a buffer at pH 5.5 and 37° C. at 1 hour≤$t_{1/2}$≤24 hours, 1 hour≤$t_{1/2}$≤1 month, and 1 hour≤$t_{1/2}$≤6 months are calculated by using Taft's equation (8), respectively. As a result, it is found that −1.71≤Σσ≤0.04 at the time of 1 hour≤$t_{1/2}$≤24 hours, −1.71≤Σσ≤0.59 at the time of 1 hour≤$t_{1/2}$≤1 month, and −1.71≤Σσ≤0.88 at the time of 1 hour≤$t_{1/2}$≤6 months, respectively.

In the case where the cyclic benzylidene acetal in formula (1) or formula (2) includes a 1,3-dioxolane structure and $R^2$ and $R^5$ are hydrogen atoms, for example, a preferred embodiment which satisfies −0.30≤Σσ≤0.21 at the time of 1 hour≤$t_{1/2}$≤24 hours is described below. However, the substituents shown herein mean $R^3$ and $R^4$ and the structures used in place of Y—$Z^1$, D-$Z^1$ and P—$Z^1$ according to the definition described above. In the preferred embodiment, one of the meta-positions in formula (1) or formula (2) is a methoxy group, an ethoxy group or an acetamide group, and more preferably an ethoxy group or an acetamide group. In another preferred embodiment, the para-position in formula (1) or formula (2) is a methoxy group or an ethoxy group and one of the meta-positions is a substituent selected from the group consisting of a fluorine atom, a chlorine atom, a bromine atom and an iodine atom, and more preferably the para-position is an ethoxy group and one of the meta-positions is a fluorine atom or a chlorine atom. In still another preferred embodiment, one of the para-position and the meta-position in formula (1) or formula (2) is a methoxy group, an ethoxy group or an acetamide group, and more preferably a methoxy group or an ethoxy group.

Moreover, in the case where the cyclic benzylidene acetal in formula (1) or formula (2) includes a 1,3-dioxolane structure and at least one of $R^2$ and $R^5$ is a substituent other than a hydrogen atom, for example, a preferred embodiment which satisfies −1.71≤Σσ≤0.04 at the time of 1 hour≤$t_{1/2}$≤24 hours is described below. However, the substituents shown herein means $R^3$ and $R^4$ and the structures used in place of Y—$Z^1$, D-$Z^1$ and P—$Z^1$ according to the definition described above. In the case where one of $R^2$ and $R^5$ in formula (1) or formula (2) is a fluorine atom, a methyl group or an ethyl group and the other is a hydrogen atom, the para-position is preferably an ethoxy group or an acetamide group, and more preferably an ethoxy group. In the case where one of $R^2$ and $R^5$ in formula (1) or formula (2) is a methoxy group and the other is a hydrogen atom, the para-position is preferably a substituent selected from the group consisting of a methoxymethyl group and an acetamide group, and more preferably an acetamide group.

Furthermore, using a numerical value derived from the compound of formula (48) described in Examples in which the hydrolysis half-life ($t_{1/2}$) in a buffer at pH 5.5 and 37° C. is 24 hours, a suitable range of the sum (Σσ) of substituent constants in the case where the cyclic benzylidene acetal in formula (1) or formula (2) includes a 1,3-dioxane structure can be defined.

In the case where the cyclic benzylidene acetal in formula (1) or formula (2) includes a 1,3-dioxane structure and $R^2$ and $R^5$ are hydrogen atoms, when the range of Σσ satisfies −0.19≤Σσ≤0.10, $t_{1/2}$ of the hydrophilic polymer derivative is represented by 1 hour≤$t_{1/2}$≤24 hours. Similarly, when the ranges of Σσ at 1 hour≤$t_{1/2}$≤1 month and 1 hour≤$t_{1/2}$≤6 months are calculated, −0.19≤Σσ≤0.41 at the time of 1 hour≤$t_{1/2}$≤1 month and −0.19≤Σσ≤0.57 at the time of 1 hour≤$t_{1/2}$≤6 months, respectively.

Moreover, in the case where the cyclic benzylidene acetal in formula (1) or formula (2) includes a 1,3-dioxone structure and at least one of $R^2$ and $R^5$ is a substituent other than a hydrogen atom, using the position constants (Es) of a phenyl group which has the largest influence of steric hindrance and a fluorine atom which has the smallest influence of steric hindrance among the substituents described above, the ranges of Σσ in a buffer at pH 5.5 and 37° C. at 1 hour≤$t_{1/2}$≤24 hours, 1 hour≤$t_{1/2}$≤1 month, and 1 hour≤≤6 months are calculated by using Taft's equation (8), respectively. As a result, it is found that −0.98≤Σσ≤0.00 at the time of 1 hour≤$t_{1/2}$≤24 hours, −0.98≤Σσ≤0.31 at the time of 1 hour≤$t_{1/2}$≤1 month, and −0.98≤Σσ≤0.48 at the time of 1 hour≤$t_{1/2}$≤6 months, respectively.

As described above, the kind and position of the substituent(s) suitable for imparting the desired hydrolyzability to the antibody-drug conjugate having a cyclic benzylidene acetal linker of the invention can be reasonably set by performing the calculation described above using equation (7) and equation (8).

(A) Antibody-Drug Conjugate Having Cyclic Benzylidene Acetal Linker

The antibody-drug conjugate of the invention can be represented by formula (1) or formula (2).

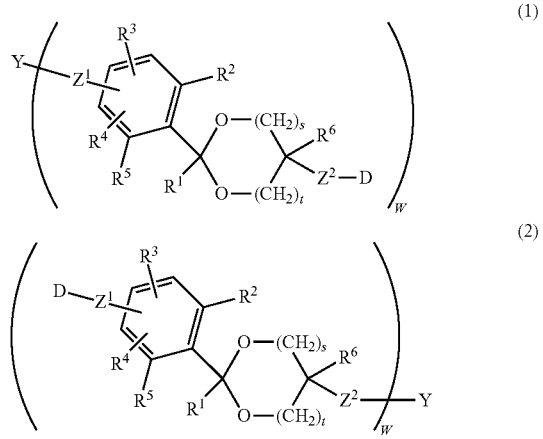

In formula (1) and formula (2), Y is an antibody, D is a drug, w is a number of drugs bound to the antibody through a cyclic benzylidene acetal linker, and $Z^1$ and $Z^2$ are each independently a selected divalent spacer.

The term "antibody" as used in the specification is used in its broadest sense and specifically covers a monoclonal antibody, a polyclonal antibody, a dimer, a multimer, a multispecific antibody (for example, a bispecific antibody) and an antibody fragment, as far as it exhibits the desired biological activity (Miller, K. et al. J. Immunol. 2003, 170, 4854-4861). The antibody can be a mouse antibody, a human antibody, a humanized antibody or a chimeric antibody, or can be derived from other species. The antibody is a protein generated by the immune system, which is capable of recognizing and binding to a specific antigen (Janeway, C.; Travers, P.; Walport, M.; Shlomchik, M. Immunobiology, 5th ed.; Garland Publishing: New York, 2001). A target antigen generally has numerous binding sites (also called epitopes) recognized by CDRs on multiple antibodies. An antibody which specifically binds to a different epitope has a different structure. Therefore, one antigen may have more than one corresponding antibody. The antibody includes the full-length immunoglobulin molecule or an immunologically active portion of a full-length immunoglobulin molecule (that is, a molecule containing an antigen binding site which immunospecifically binds to an antigen of interest or part thereof). Such a target includes a cancer cell and a cell which generates an autoimmune antibody associated with an autoimmune disease, but it is not limited thereto. The immunoglobulin disclosed in the specification may be of any type (for example, IgG, IgE, IgM, IgD or IgA), class (for example, IgG1, IgG2, IgG3, IgG4, IgA1 or IgA2) or subclass thereof. The immunoglobulin may be derived from any species. However, in one embodiment, the immunoglobulin is of human origin, mouse origin or rabbit origin.

The polyclonal antibody is a heterogeneous population of antibody molecules, for example, that derived from the serum of immunized animal. The polyclonal antibody to an antigen of interest may be produced using known various procedures in the art. For example, in order to produce a polyclonal antibody, various host animals including, but not limited to, rabbit, mouse, rat and guinea pig, may be immunized by injection with an antigen of interest or derivative thereof. The immunological response may be increased by using various adjuvants including, but not limited to, Freund's (complete and incomplete) adjuvant, a mineral gel, for example, aluminum hydroxide, a surface active substance, for example, lysolecithin, a pluronic polyol, a polyanion, a peptide, an oil emulsion, keyhole limpet hemocyanin, dinitrophenol, and a potentially useful human adjuvant, for example, BCG (Bacille Calmett-Guerin) or *Corynebacterium parvum*, depending on the host species. Such adjuvants are also well known in the art.

The monoclonal antibody is a homogeneous population of antibodies to a specific antigenic determinant (for example, a cell antigen (cancer or autoimmune cell antigen), a viral antigen, a microbial antigen, a protein, a peptide, a carbohydrate, a chemical substance, a nucleic acid or antigen-binding fragments thereof). A monoclonal antibody (mAb) to an antigen of interest may be prepared by using any technique known in the art. These include, but are not limited to, the hybridoma technique originally described by Kohler, G; Milstein, C. Nature 1975, 256, 495-497, the human B cell hybridoma technique (Kozbor, D. et al. Immunol. Today 1983, 4, 72-79) and the EBV-hybridoma technique (Cole, S. P. et al. Monoclonal Antibodies and Cancer Therapy; Alan R. Liss: New York, 1985, pp. 77-96). Such antibodies may be of any immunoglobulin class including IgG, IgM, IgE, IgA and IgD and any subclass thereof. The hybridoma producing the monoclonal antibody in the invention may be cultivated in vitro or in vivo.

The monoclonal antibody includes, but is not limited to, a human monoclonal antibody, a humanized monoclonal antibody, a chimeric monoclonal antibody and an antibody fragment. The human monoclonal antibody may be made by any of numerous techniques known in the art (see, for example, Teng, N. N. et al. Proc. Natl. Acad. Sci. USA. 1983, 80, 7308-7312, Kozbor, D. et al. Immunology Today 1983, 4, 72-79, Olsson L. et al. Meth. Enzymol. 1982, 92, 3-16, and U.S. Pat. Nos. 5,939,598 and 5,770,429). A recombinant antibody, for example, a chimeric monoclonal antibody or a humanized monoclonal antibody can be made using standard recombinant DNA techniques known in the art (see, for example, U.S. Pat. Nos. 4,816,567 and 4,816,397).

The immunogenicity of the antibody can also be reduced by the surface reconstruction (resurfacing) treatment of the antibody (see, U.S. Pat. No. 5,225,539 and European Patents 0239400, 0519596 and 0592106).

In one embodiment of the invention, the antibody may be a bispecific antibody. Methods for making the bispecific antibody are known in the art. Conventional production method of full-length bispecific antibody utilizes the simultaneous expression of two immunoglobulin heavy chain-light chain pairs in which the two chains have different specificities (see, Milstein, C. et al. Nature 1983, 305, 537-539). According to a different method, the bispecific antibody can also be produced by fusing an antibody variable domain with the desired binding specificity (antibody-antigen binding site) to an immunoglobulin constant domain sequence.

Other useful antibodies include fragments of antibodies, but are not limited to, F(ab')$_2$ fragment, Fab' fragment, Fab fragment, Fvs, a single chain antibody (SCA) (for example, as described in U.S. Pat. No. 4,946,778, Bird, R. E. et al. Science 1988, 242, 423-442, Huston, J. S. et al. Proc. Natl.

Acad. Sot USA 1988, 85, 5879-5883, and Ward, E. S. et al. Nature 1989, 334, 544-554), scFv, sc-Fv-Fc, FvdsFv, minibody, diabody, triabody, tetrabody, and any other molecule containing CDR and having the same specificity as the antibody, for example, a domain antibody.

In a preferred aspect of the invention, a known antibody for the treatment or prevention of cancer may be used. All target proteins including any target protein whose expression is correlated with expression on cells of a cancer, cell proliferative disorder or tumor can be targeted by an antibody.

In a preferred embodiment of the invention, the antibody is useful for the treatment of cancer. Examples of the antibody useful for the treatment of cancer include, but are not limited to, RITUXAN (registered trademark) (Genentech Inc.) which is a chimeric anti-CD20 monoclonal antibody for the treatment of patient with non-Hodgkin's lymphoma, OVAREX (AltaRex Corp.) which is a mouse antibody for the treatment of ovarian cancer, PANOREX (Glaxo Wellcome Inc.) which is a mouse $IgG2_a$ antibody for the treatment of colorectal cancer, CETUXIMAB ERBITUX (ImClone Systems Inc.) which is an anti-EGFR IgG chimeric antibody for the treatment of epidermal growth factor positive cancer, for example, head cancer or neck cancer, VITAXIN (MedImmune Inc.) which is a humanized antibody for the treatment of sarcoma, CAMPATH I/H (Leukosite Inc.) which is a humanized IgG1 antibody for the treatment of chronic lymphocytic leukemia (CLL), Smart M195 (Protein Design Labs Inc.) which is a humanized anti-CD33 IgG antibody for the treatment of acute myeloid leukemia (AML), LYMPHOCIDE (Immunomedics Inc.) which is a humanized anti-CD22 IgG antibody for the treatment of non-Hodgkin's lymphoma, Smart ID10 (Protein Design Labs Inc.) which is a humanized anti-HLA-DR antibody for the treatment of non-Hodgkin's lymphoma, Oncolym (Techniclone Inc.) which is a radiolabeled mouse anti-HLA-Dr10 antibody for the treatment of non-Hodgkin's lymphoma, ALLOMUNE (BioTransplant Inc.) which is a humanized anti-CD2 mAb for the treatment of Hodgkin's disease or non-Hodgkin's lymphoma, AVASTIN (Genentech Inc.) which is an anti-VEGF humanized antibody for the treatment of lung cancer and colorectal cancer, Epratuzamab (Immunomedics Inc. and Amgen Inc.) which is an anti-CD22 antibody for the treatment of non-Hodgkin's lymphoma, and CEAcide (Immunomedics Inc.) which is a humanized anti-CEA antibody for the treatment of colorectal cancer.

In a preferred embodiment of the invention, the antibody is an antibody to the following antigens: CA125, CA15-3, CA19-9, L6, Lewis Y, Lewis X, alpha fetoprotein, CA242, placental alkaline phosphatase, prostate specific membrane antigen, EphB2, TMEFF2, prostatic acid phosphatase, epidermal growth factor, MAGE-1, MAGE-2, MAGE-3, MAGE-4, anti-transferrin receptor, p97, MUC1-KLH, CEA, gp 100, MART 1, prostate specific antigen, IL-2 receptor, CD20, CD52, CD33, CD22, human chorionic gonadotropin, CD38, CD40, mucin, P21, MPG and Neu oncogene product. Some specific useful antibodies include, but are not limited to, mAb to the CD40 antigen, for example, BR96 mAb (Trail, P. A. et al. Science 1993, 261, 212-215), BR64 (Trail, P. A. et al. Cancer Research 1997, 57, 100-105) or S2C6 mAb (Francisco, J. A. et al. Cancer Res. 2000, 60, 3225-3231) or other anti-CD40 antibodies, for example, as those disclosed in U.S. Patent Application Publication Nos. 2003/0211100 and 2002/0142358, mAb to the CD70 antigen, for example, 1F6 mAb and 2F2 mAb, and mAb to the CD30 antigen, for example, AC10 (Bowen, M. A. et al. J. Immunol. 1993, 151, 5896-5906, Wahl, A. F. et al. Cancer Res. 2002, 62(13), 3736-3742) or MDX-0060 (U.S. Patent Application Publication No. 2004/0006215).

The drug which can be used in the invention includes a chemotherapeutic agent. The chemotherapeutic agent is a compound useful in the treatment of cancer. Examples of the chemotherapeutic agent include the followings: alkylating agents, for example, thiotepa or cyclophosphamide (CYTOXAN (trademark)); alkyl sulfonates, for example, busulfan, improsulfan or piposulfan; aziridines for example, benzodopa, carboquone, meturedopa or uredopa; ethyleneimines and methylamelamines including altretamine, triethylenemelamine, triethylenephosphoramide, triethylenethiophosphoramide and trimethylolomelamine; acetogenins (particularly bullatacin and bullatacinone); camptothecin (including synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including synthetic analogs KW-2189 and CBI-TMI; eleutherobin; pancratistatin; sarcodictyin; spongistatin; nitrogen mustards, for example, chlorambucil, chlornaphazine, cholophosphamide, estramustine, ifosfamide, mechlorethamine, mechlorethamine oxide hydrochloride, melphalan, novembichin, phenesterine, prednimustine, trofosfamide or uracil mustard; nitrosoureas, for example, carmustine, chlorozotocin, fotemustine, lomustine, nimustine or ranimustine; antibiotics, for example, enediyne antibiotics (for example, calicheamicin, particularly calicheamicin gamma 1 and calicheamicin theta 1, see, for example, Angew Chem Intl. Ed. Engl. 33:183-186 (1994); dynemicin (including dynemicin A); esperamicin; or neocarzinostatin chromophore and related chromoprotein enediyne antibiotic chromophores), aclacinomysins, actinomycin, authramycin, azaserine, bleomycins, cactinomycin, carabicin, carminomycin, carzinophilin, chromomycins, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, nitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites, for example, methotrexate or 5-fluorouracil (5-FU); folic acid analogs, for example, demopterin, methotrexate, pteropterin or trimetrexate; purine analogs, for example, fludarabine, 6-mercaptopurine, thiamiprine or thioguanine; pyrimidine analogs, for example, ancitabine, azacitidine, 6-azauridine, carmofur, cytarabine, dideoxyuridine, doxifluridine, enocitabine, floxuridine or 5-FU; androgens, for example, calusterone, dromostanolone propionate, epitiostanol, mepitiostane or testolactone; anti-adrenals, for example, aminoglutethimide, mitotane or trilostane; folic acid replenisher, for example, frolinic acid; aceglatone; aldophosphamide glycoside; aminolevulinic acid; amsacrine; bestrabucil; bisantrene; edatraxate; defofamine; demecolcine; diaziquone; elfomithine; elliptinium acetate; epothilone; etogiucid; gallium nitrate; hydroxy urea; lentinan; lonidamine; maytansinoids, for example, maytansine or ansamitocins; mitoguazone; mitoxantrone; mopidamol; nitracrine; pentostatin; phenamet; pirarubicin; podophyllinic acid; 2-ethylhydrazide; procarbazine; PSK (registered trademark); razoxane; rhizoxin; sizofiran; spirogermanium; tenuazonic acid; triaziquone; 2,2',2"-trichlorotriethylamine; trichothecenes (particularly T-2 toxin, verracurin A, roridin A and anguidine); urethane; vindesine; dacarbazine; mannomustine; mitobronitol; mitolactol; pipobroman; gacytosine; arabinoside ("Ara-C"); cyclophosphamide; thiotepa; taxoids, for example, paclitaxel (TAXOL (registered trademark), Bristol-Myers Squibb Oncology) or doxetaxel (TAXOTERE (registered trademark), Rhone-Poulenc Rorer); chlorambucil; gemcitabine; 6-thioguanine; mercaptopurine; methotrexate; platinum analogs, for example, cisplatin or carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylomithine (DMFO); retinoic acid; capecitabine; and pharmaceutically acceptable salts, acids or derivatives of any of those described above. Anti-hormonal agents which act to regulate or inhibit hormone action on tumors, for example, anti-estrogen drugs including, for example, tamoxifen, raloxifene, 4(5)-imidazoles inhibiting aromatase, 4-hydroxytamoxifen, trioxifene, keoxifene, LY 117018, onapristone and toremifene (Fareston); and anti-androgen drugs, for example, flutamide, nilutamide, bicalutamide, leuprolide or goserelin; siRNA, and pharmaceutically acceptable salts, acids or derivatives of any of those described above are also included in the definition. Other chemotherapeutic agents which can be used with the invention are disclosed in U.S. Patent Application Publication Nos. 2008/0171040 and 2008/0305044, all of which are incorporated by reference in their entirety herein.

In a preferred aspect of the invention, the chemotherapeutic agent is a low molecular drug. The low molecular drug has a molecular weight preferably from 100 to 1,500, more preferably from 120 to 1,200, and still more preferably from 200 to 1,000. Typically, as the low molecular drug, organic, inorganic or organometallic compounds having a molecular weight of less than about 1,000 is widely used. The low molecular drugs of the invention also include oligopeptides and other biomolecules each having a molecular weight of less than about 1,000. The low molecular drugs are well characterized in the art, for example, especially in WO 05/058367, EP-A-85901495, EP-A-8590319 and U.S. Pat. No. 4,956,303, all of which are incorporated by reference in their entirety herein.

A preferred low molecular drug of the invention is a low molecular drug capable of being linked to the antibody. The invention includes known drugs as well as those which may become known. Particularly preferred low molecular drugs include a cytotoxic agent.

Preferred cytotoxic agents include maytansinoids, CC-1065 analogues, morpholinos, doxorubicins, taxanes, crtptophycins, epothilones, calicheamicins, auristatins and pyrrolobenzodiazepine dimers.

The number of the drug (D) bound to the antibody (Y) through the cyclic benzylidene acetal linker is represented by w in formula (1) or formula (2), and is defined as an average number of the drugs per antibody. w is from 1 to 20. w is preferably 2 or more, and more preferably 3 or more. Also, w is preferably 15 or less, more preferably 10 or less, and particularly preferably 8 or less.

The average number w of the drugs per antibody in the ADC can be determined by methods known to those skilled in the art, for example, ultraviolet/visible spectroscopy method, mass spectrometry method, ELISA method, electrophoresis, HPLC, and a method of combination thereof.

$Z^1$ or $Z^2$ in formula (1) or formula (2) is a divalent spacer between the benzene ring of the cyclic benzylidene acetal and the antibody or a divalent spacer between the acetal group and the drug. These are composed of covalent bonds, are not particularly limited as far as they are more stable to acid hydrolysis than the cyclic benzylidene acetal group, and are preferably an ether bond, an ester bond, a carbonate bond, a urethane bond, an amide bond, a thioether bond, a disulfide bond, a 1H-1,2,3-triazole-1,4-diyl group, a secondary amino group, an aliphatic hydrocarbon group containing any of these bonds and groups, a single bond or an aliphatic hydrocarbon group. The number of carbon atoms of the aliphatic hydrocarbon group is preferably from 1 to 24. By way of illustration and without limitation, preferred examples of the aliphatic hydrocarbon group include structures such as (z1). Preferred examples of the aliphatic hydrocarbon group having an ether bond include structures such as (z2) or (z3). Preferred examples of the aliphatic hydrocarbon group having an ester bond include structures such as (z4). Preferred examples of the aliphatic hydrocarbon group having a carbonate bond include structures such as (z5). Preferred examples of the aliphatic hydrocarbon group having a urethane bond include structures such as (z6). Preferred examples of the aliphatic hydrocarbon group having an amide bond include structures such as (z7). Preferred examples of the aliphatic hydrocarbon group having a secondary amino group include structures such as (z8). Preferred examples of the aliphatic hydrocarbon group having a thioether bond include structures such as (z9). Preferred examples of the aliphatic hydrocarbon group having a disulfide bond include structures such as (z10). Preferred examples of the aliphatic hydrocarbon group having a 1H-1,2,3-triazole-1,4-diyl group include structures such as (z11). In a preferred embodiment, p and q are each independently an integer of 1 to 12. However, in the case where at least one of $Z^1$ and $Z^2$ is an ether bond, an ester bond, a carbonate bond, a urethane bond, an amide bond, a thioether bond, a disulfide bond, a 1H-1,2,3-triazole-1,4-diyl group, a secondary amino group or an aliphatic hydrocarbon group containing any of these bonds and groups and a plurality of identical structural units are bound, a number of the structural units described above is 2 or less.

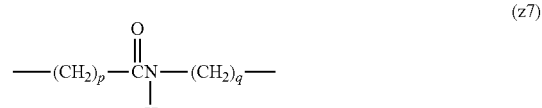
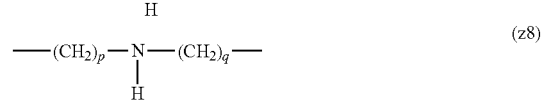

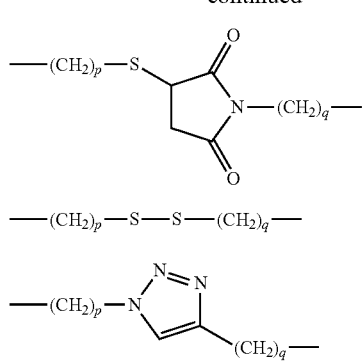

(z9)

(z10)

(z11)

The antibody-drug conjugate of formula (1) is divided into w pieces of drug fragments and one antibody fragment by hydrolysis of the cyclic benzylidene acetal linker as illustrated in the scheme shown below.

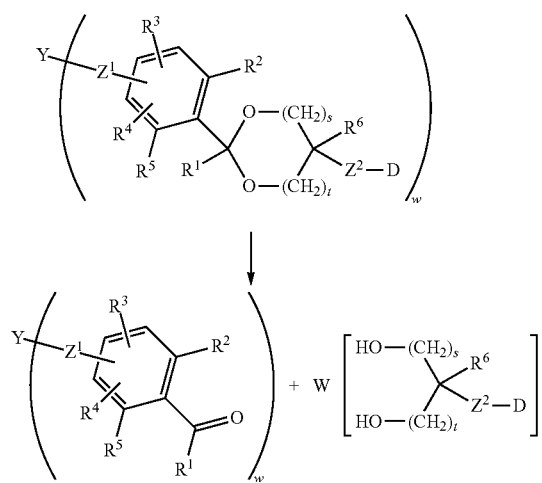

The antibody-drug conjugate of formula (2) is divided into w pieces of drug fragments and one antibody fragment by hydrolysis of the cyclic benzylidene acetal linker as illustrated in the scheme shown below.

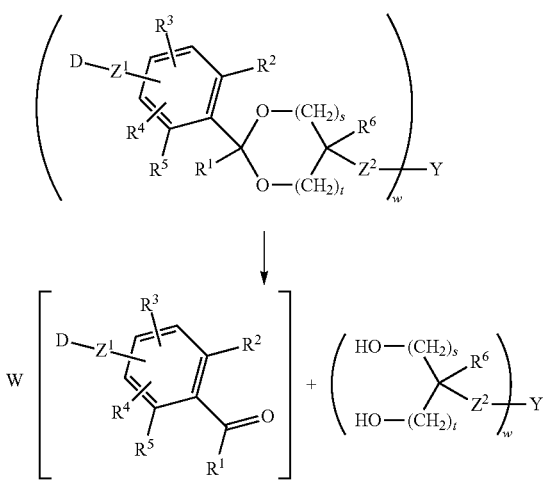

(B) Antibody Having Cyclic Benzylidene Acetal Linker Bound Thereto

According to one aspect of the invention, the antibody-drug conjugate represented by formula (1) or formula (2) can be synthesized by linking an antibody having a cyclic benzylidene acetal linker bound thereto to a drug. The antibody having a cyclic benzylidene acetal linker bound thereto is a compound represented by formula (3) or formula (4) shown below.

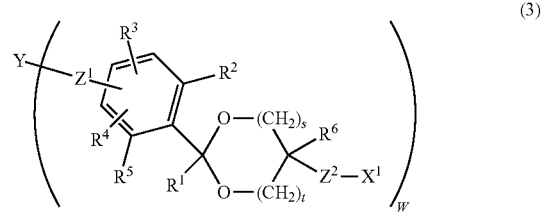

(3)

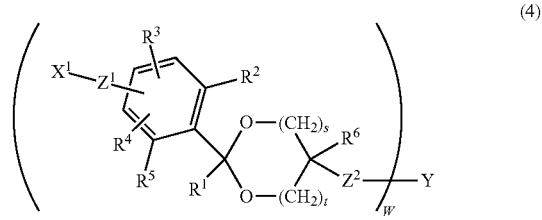

(4)

In formula (3) and formula (4), Y is an antibody, $X^1$ is a reactive functional group capable of linking to a drug by a covalent bond, w is a number of cyclic benzylidene acetal linkers bound to the antibody, and $Z^3$ and $Z^4$ are each independently a selected divalent spacer.

$X^1$ in formula (3) or formula (4) of the invention is not particularly limited as far as it is a reactive functional group which reacts with a functional group present on the drug to be linked to form a covalent bond. The reactive functional group includes those described, for example, in "Hermanson, G T. Bioconjugate Techniques, 2nd ed.; Academic Press: San Diego, Calif., 2008", "Harris, J. M. Poly(Ethyleneglycol) Chemistry; Plenum Press: New York, 1992", and "PEGylatedProtein Drugs: Basic Science and Clinical Applications; Veronese, F. M., Ed.; Birkhauser: Basel, Switzerland, 2009".

Preferred examples of $X^1$ include an active ester group, an active carbonate group, an aldehyde group, an isocyanate group, an isothiocyanate group, an epoxy group, a maleimide group, a vinyl sulfone group, an acryl group, a sulfonyloxy group, a carboxyl group, a thiol group, a dithiopyridyl group, an α-haloacetyl group, an alkynyl group, an allyl group, a vinyl group, an amino group, an oxyamino group, a hydrazide group, an azide group, a hydroxyl group, a dibenzocyclooctyne group and a bicyclo[6.1.0]nonyne group. In a more specific embodiment, the functional group capable of forming a covalent bond upon a reaction with an amino group of the reaction partner is an active ester group, an active carbonate group, an aldehyde group, an isocyanate group, an isothiocyanate group, an epoxy group, a maleimide group, a vinyl sulfone group, an acryl group, a sulfonyloxy group or a carboxyl group, the functional group capable of forming a covalent bond upon a reaction with a thiol group of the reaction partner is an active ester group, an active carbonate group, an aldehyde group, an isocyanate group, an isothiocyanate group, an epoxy group, a maleimide group, a vinyl sulfone group, an acryl group, a sulfonyloxy group, a carboxyl group, a thiol group, a dithiopyridyl group, an α-haloacetyl group, an alkynyl group, an allyl group or a vinyl group, the functional group capable of forming a covalent bond upon a reaction with an aldehyde group or a carboxyl group of the reaction partner is a thiol group, an amino group, an oxyamino group or a hydrazide group, the functional group capable of forming a covalent bond upon a reaction with an alkynyl group of the reaction partner is a thiol group or an azide group, the functional group capable of forming a covalent bond upon a reaction with an azide group of the reaction partner is an alkynyl group, a dibenzocyclooctyne group or a bicyclo[6.1.0]nonyne group, and the functional group capable of forming a covalent bond upon a reaction with a halogenated alkyl group, an alkyl sulfonic acid ester or an aryl sulfonic acid ester of the reaction partner is a hydroxyl group, a thiol group or an amino group.

The term "active ester" as referred to herein indicates an activated carboxy group represented by formula: —C(=O)-L, wherein L represents a leaving group. The leaving group represented by L includes a succinimidyloxy group, a phthalimidyloxy group, a 4-nitrophenoxy group, a 1-imidazolyl group, a pentafluorophenoxy group, a benzotriazol-1-yloxy group, a 7-azabenzotriazol-1-yloxy group and the like. The term "active carbonate" as referred to herein indicates an activated carbonate group represented by formula: —O—C(=O)-L, wherein L represents the leaving group same as described above.

In a preferred embodiment of the aspect, X' is a group represented by group (I), group (II), group (III), group (IV), group (V) or group (VI).

Group (I): Functional group capable of forming a covalent bond upon a reaction with an amino group of the reaction partner
  (a), (b), (c), (d), (e) and (f) shown below:
Group (II): Functional group capable of forming a covalent bond upon a reaction with a thiol group of the reaction partner
  (a), (b), (c), (d), (e), (f), (g), (h), (i) and (j) shown below:
Group (III): Functional group capable of forming a covalent bond upon a reaction with an aldehyde group or a carboxyl group of the reaction partner
  (g), (k), (l) and (m) shown below:
Group (IV): Functional group capable of forming a covalent bond upon a reaction with an alkynyl group of the reaction partner
  (g), (k), (l), (m) and (n) shown below:
Group (V): Functional group each capable of forming a covalent bond upon a reaction with an azide group of the reaction partner
  (j), (p) and (q) shown below:
Group (VI): Functional group each capable of forming a covalent bond upon a reaction with a halogenated alkyl group, an alkyl sulfonic acid ester or an aryl sulfonic acid ester of the reaction partner
  (o), (g) and (k) shown below:

In the formulae above, $R^7$ is a hydrogen atom or a sulfo group, specific examples of the sulfo group include sodium sulfonate and potassium sulfonate, and $R^7$ is preferably a hydrogen atom. $R^8$ and $R^{11}$ are each a hydrogen atom or a hydrocarbon group having from 1 to 5 carbon atoms, and specific examples of the hydrocarbon group include a methyl group, an ethyl group, a propyl group, an isopropyl group, a butyl group, a tert-butyl group and a pentyl group. $R^9$ is a hydrocarbon group having from 1 to 10 carbon atoms which may contain a halogen atom, specific examples of the hydrocarbon group include a methyl group, an ethyl group, a propyl group, an isopropyl group, a butyl group, a tert-butyl group, a pentyl group, an isopentyl group, a hexyl group, a benzyl group, a 4-methylphenyl group, a trifluoromethyl group, a 2,2,2-trifluoroethyl group, a 4-(trifluoromethoxy)phenyl group, a vinyl group, a chloroethyl group, a bromoethyl group and an iodoethyl group, and $R^9$ is preferably a methyl group, a vinyl group, a 4-methylphenyl group or a 2,2,2-trifluoroethyl group. $R^{10}$ is a halogen atom selected from the group consisting of a chlorine atom, a bromine atom and an iodine atom.

$Z^3$ in formula (3) is a divalent spacer between the acetal group of the cyclic benzylidene acetal and $X^1$, and $Z^4$ in formula (4) is a divalent spacer between the benzene ring and $X^1$. These are composed of covalent bonds, are not particularly limited as far as they are more stable to acid hydrolysis than the cyclic benzylidene acetal group, and are preferably an ether bond, an ester bond, a carbonate bond, a urethane bond, an amide bond, a thioether bond, a disulfide bond, a 1H-1,2,3-triazole-1,4-diyl group, a secondary amino group, an aliphatic hydrocarbon group containing any of these bonds and groups, a single bond or an aliphatic hydrocarbon group. The number of carbon atoms of the aliphatic hydrocarbon group is preferably from 1 to 24. By way of illustration and without limitation, preferred examples of the aliphatic hydrocarbon group include structures such as (z1). Preferred examples of the aliphatic hydrocarbon group having an ether bond include structures such as (z2) or (z3). Preferred examples of the aliphatic hydrocarbon group having an ester bond include structures such as (z4). Preferred examples of the aliphatic hydrocarbon group having a carbonate bond include structures such as (z5). Preferred examples of the aliphatic hydrocarbon group having a urethane bond include structures such as (z6). Preferred examples of the aliphatic hydrocarbon group having an amide bond include structures such as (z7). Preferred examples of the aliphatic hydrocarbon group having a secondary amino group include structures such as (z8). Preferred examples of the aliphatic hydrocarbon group having a thioether bond include structures such as (z9). Preferred examples of the aliphatic hydrocarbon group having a disulfide bond include structures such as (z10). Preferred examples of the aliphatic hydrocarbon group having a 1H-1,2,3-triazole-1,4-diyl group include structures such as (z11). In a preferred embodiment, p and q are each independently an integer of 1 to 12. However, in the case where at least one of $Z^3$ and $Z^4$ is an ether bond, an ester bond, a carbonate bond, a urethane bond, an amide bond, a thioether bond, a disulfide bond, a 1H-1,2,3-triazole-1,4-diyl group, a secondary amino group or an aliphatic hydrocarbon group containing any of these bonds and groups and a plurality of identical structural units are bound, a number of the structural units described above is 2 or less.

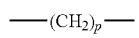 (z1)

 (z2)

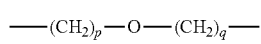 (z3)

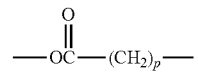 (z4)

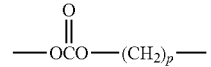 (z5)

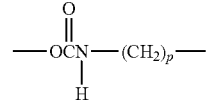 (z6)

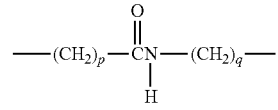 (z7)

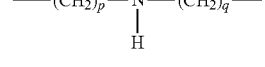 (z8)

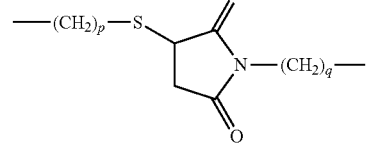 (z9)

 (z10)

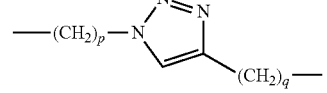 (z11)

According to a preferred embodiment of the invention, prior to linking the compound of formula (3) or formula (4) to a drug, the functional group present on the drug is chemically converted into another functional group, and then the functional group chemically converted is reacted with $X^1$ of formula (3) or formula (4), thereby synthesizing the antibody-drug conjugate of formula (1) or formula (2). Preferred examples of the functional group of the drug after the chemical conversion include groups wherein the linkage formed by the reaction between the functional group and $X^1$ is an ether bond, an ester bond, a carbonate bond, a urethane bond, an amide bond, a thioether bond, a disulfide bond, a 1H-1,2,3-triazole-1,4-diyl group, a secondary amino group, an aliphatic hydrocarbon group containing any of these bonds and groups, a single bond or an aliphatic hydrocarbon group included in $Z^1$ or $Z^2$ of formula (1) or formula (2), and specifically include, for example, a halogen atom, an active ester, an active carbonate, an aldehyde group, an amino group, a hydroxyl group, a carboxyl group, a thiol group, an alkynyl group and an azide group.

According to another preferred embodiment of the invention, the functional group present on the drug is reacted with one of the reactive functional groups of a bifunctional cross-linker, and the other reactive functional group of the cross linker is reacted with $X^1$ of formula (3) or formula (4), thereby synthesizing the antibody-drug conjugate of formula (1) or formula (2). Specific examples of the cross-linker can be found in a large number of general books and described, for example, in "Hermanson, G T. Bioconjugate Techniques, 2nd ed.; Academic Press: San Diego, Calif., 2008". Preferred examples of the reactive functional group of the cross linker include groups wherein the linkages formed by the reactions between the functional group and the drug and between the reactive functional group and $X^1$ are an ether bond, an ester bond, a carbonate bond, a urethane bond, an amide bond, a thioether bond, a disulfide bond, a 1H-1,2,3-triazole-1,4-diyl group, a secondary amino group, an aliphatic hydrocarbon group containing any of these bonds and groups, a single bond or an aliphatic hydrocarbon group included in $Z^1$ or $Z^2$ of formula (1) or formula (2), and specifically include a halogen atom, an active ester, an active carbonate, an aldehyde group, an amino group, a hydroxyl group, a carboxyl group, a thiol group, a maleimide group, an alkynyl group and an azide group.

(C) Drug Having Cyclic Benzylidene Acetal Linker Bound Thereto

According to another aspect of the invention, the antibody-drug conjugate represented by formula (1) or formula (2) can be synthesized by linking a drug having a cyclic benzylidene acetal linker bound thereto to an antibody. The drug having a cyclic benzylidene acetal linker bound thereto is a compound represented by formula (5) or formula (6) shown below.

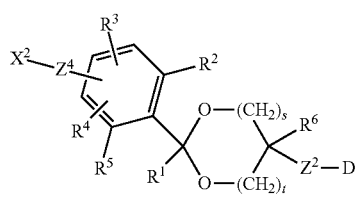

(5)

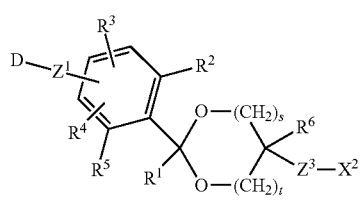

(6)

In formula (5) and formula (6), D is a drug, $X^2$ is a reactive functional group capable of linking to an antibody by a covalent bond, and $Z^3$ and $Z^4$ are each independently a selected divalent spacer.

$X^2$ in formula (5) or formula (6) of the invention is not particularly limited as far as it is a reactive functional group which reacts with a functional group present on the antibody to be linked to form a covalent bond. The reactive functional group includes those described, for example, in "Hermanson, G T. Bioconjugate Techniques, 2nd ed.; Academic Press: San Diego, Calif., 2008", "Harris, J. M. Poly(Ethyleneglycol) Chemistry; Plenum Press: New York, 1992", and "PEGylatedProtein Drugs: Basic Science and Clinical Applications; Veronese, F. M., Ed.; Birkhauser: Basel, Switzerland, 2009".

Preferred examples of $X^2$ include an active ester group, an active carbonate group, an aldehyde group, an isocyanate group, an isothiocyanate group, an epoxy group, a maleimide group, a vinyl sulfone group, an acryl group, a sulfonyloxy group, a carboxyl group, a thiol group, a dithiopyridyl group, an α-haloacetyl group, an alkynyl group, an allyl group, a vinyl group, an amino group, an oxyamino group, a hydrazide group, an azide group, a hydroxyl group, a dibenzocyclooctyne group and a bicyclo[6.1.0]nonyne group. In a more specific embodiment, the functional group capable of forming a covalent bond upon a reaction with an amino group of the reaction partner is an active ester group, an active carbonate group, an aldehyde group, an isocyanate group, an isothiocyanate group, an epoxy group, a maleimide group, a vinyl sulfone group, an acryl group, a sulfonyloxy group or a carboxyl group, the functional group capable of forming a covalent bond upon a reaction with a thiol group of the reaction partner is an active ester group, an active carbonate group, an aldehyde group, an isocyanate group, an isothiocyanate group, an epoxy group, a maleimide group, a vinyl sulfone group, an acryl group, a sulfonyloxy group, a carboxyl group, a thiol group, a dithiopyridyl group, an α-haloacetyl group, an alkynyl group, an allyl group or a vinyl group, the functional group capable of forming a covalent bond upon a reaction with an aldehyde group or a carboxyl group of the reaction partner is a thiol group, an amino group, an oxyamino group or a hydrazide group, the functional group capable of forming a covalent bond upon a reaction with an alkynyl group of the reaction partner is a thiol group or an azide group, the functional group capable of forming a covalent bond upon a reaction with an azide group of the reaction partner is an alkynyl group, a dibenzocyclooctyne group or a bicyclo[6.1.0]nonyne group, and the functional group capable of forming a covalent bond upon a reaction with a halogenated alkyl group, an alkyl sulfonic acid ester or an aryl sulfonic acid ester of the reaction partner is a hydroxyl group, a thiol group or an amino group.

In a preferred embodiment of the aspect, $X^2$ is a group represented by group (I), group (II), group (III), group (IV), group (V) or group (VI).

Group (I): Functional group capable of forming a covalent bond upon a reaction with an amino group of the reaction partner (a), (b), (c), (d), (e) and (f) shown below:

Group (II): Functional group capable of forming a covalent bond upon a reaction with a thiol group of the reaction partner (a), (b), (c), (d), (e), (f), (g), (h), (i) and (j) shown below:

Group (III): Functional group capable of forming a covalent bond upon a reaction with an aldehyde group or a carboxyl group of the reaction partner (g), (k), (l) and (m) shown below:

Group (IV): Functional group capable of forming a covalent bond upon a reaction with an alkynyl group of the reaction partner (g), (k), (l), (m) and (n) shown below:

Group (V): Functional group each capable of forming a covalent bond upon a reaction with an azide group of the reaction partner (j), (p) and (q) shown below:

Group (VI): Functional group each capable of forming a covalent bond upon a reaction with a halogenated alkyl group, an alkyl sulfonic acid ester or an aryl sulfonic acid ester of the reaction partner (o), (g) and (k) shown below:

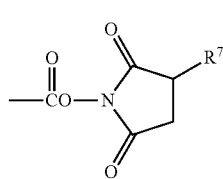

(a)

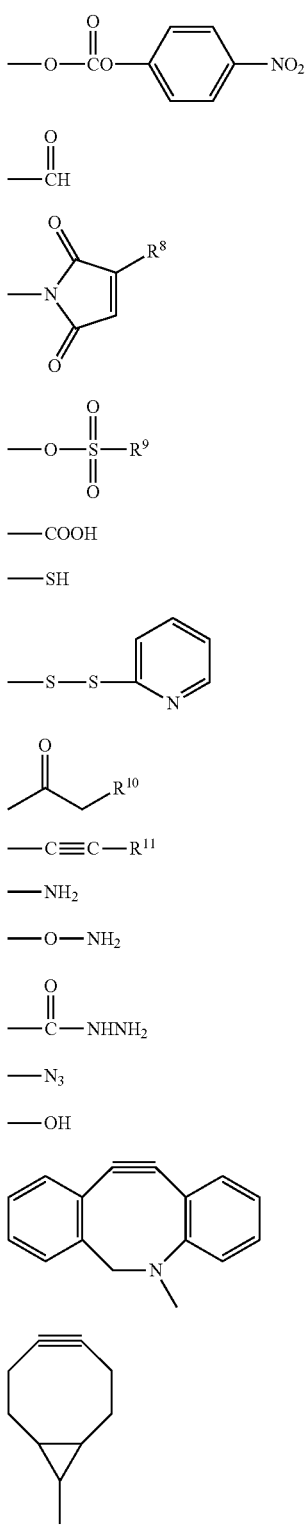

(b)
(c)
(d)
(e)
(f)
(g)
(h)
(i)
(j)
(k)
(l)
(m)
(n)
(o)
(p)
(q)

In the formulae above, $R^7$ is a hydrogen atom or a sulfo group, specific examples of the sulfo group include sodium sulfonate and potassium sulfonate, and $R^7$ is preferably a hydrogen atom. $R^8$ and $R^{11}$ are each a hydrogen atom or a hydrocarbon group having from 1 to 5 carbon atoms, and specific examples of the hydrocarbon group include a methyl group, an ethyl group, a propyl group, an isopropyl group, a butyl group, a tert-butyl group and a pentyl group. $R^9$ is a hydrocarbon group having from 1 to 10 carbon atoms which may contain a halogen atom, specific examples of the hydrocarbon group include a methyl group, an ethyl group, a propyl group, an isopropyl group, a butyl group, a tert-butyl group, a pentyl group, an isopentyl group, a hexyl group, a benzyl group, a 4-methylphenyl group, a trifluoromethyl group, a 2,2,2-trifluoroethyl group, a 4-(trifluoromethoxy)phenyl group, a vinyl group, a chloroethyl group, a bromoethyl group and an iodoethyl group, and $R^9$ is preferably a methyl group, a vinyl group, a 4-methylphenyl group or a 2,2,2-trifluoroethyl group. $R^{10}$ is a halogen atom selected from the group consisting of a chlorine atom, a bromine atom and an iodine atom.

$Z^4$ in formula (5) is a divalent spacer between the benzene ring of the cyclic benzylidene acetal and $X^2$, and $Z^3$ in formula (6) is a divalent spacer between the acetal group and $X^2$. These are composed of covalent bonds, are not particularly limited as far as they are more stable to acid hydrolysis than the cyclic benzylidene acetal group, and are preferably an ether bond, an ester bond, a carbonate bond, a urethane bond, an amide bond, a thioether bond, a disulfide bond, a 1H-1,2,3-triazole-1,4-diyl group, a secondary amino group, an aliphatic hydrocarbon group containing any of these bonds and groups, a single bond or an aliphatic hydrocarbon group. The number of carbon atoms of the aliphatic hydrocarbon group is preferably from 1 to 24. By way of illustration and without limitation, preferred examples of the aliphatic hydrocarbon group include structures such as (z1). Preferred examples of the aliphatic hydrocarbon group having an ether bond include structures such as (z2) or (z3). Preferred examples of the aliphatic hydrocarbon group having an ester bond include structures such as (z4). Preferred examples of the aliphatic hydrocarbon group having a carbonate bond include structures such as (z5). Preferred examples of the aliphatic hydrocarbon group having a urethane bond include structures such as (z6). Preferred examples of the aliphatic hydrocarbon group having an amide bond include structures such as (z7). Preferred examples of the aliphatic hydrocarbon group having a secondary amino group include structures such as (z8). Preferred examples of the aliphatic hydrocarbon group having a thioether bond include structures such as (z9). Preferred examples of the aliphatic hydrocarbon group having a disulfide bond include structures such as (z10). Preferred examples of the aliphatic hydrocarbon group having a 1H-1,2,3-triazole-1,4-diyl group include structures such as (z11). In a preferred embodiment, p and q are each independently an integer of 1 to 12. However, in the case where at least one of $Z^3$ and $Z^4$ is an ether bond, an ester bond, a carbonate bond, a urethane bond, an amide bond, a thioether bond, a disulfide bond, a 1H-1,2,3-triazole-1,4-diyl group, a secondary amino group or an aliphatic hydrocarbon group containing any of these bonds and groups and a plurality of identical structural units are bound, a number of the structural units described above is 2 or less.

—(CH$_2$)$_p$— (z1)

—O(CH$_2$)$_p$— (z2)

—(CH$_2$)$_p$—O—(CH$_2$)$_q$— (z3)

-continued

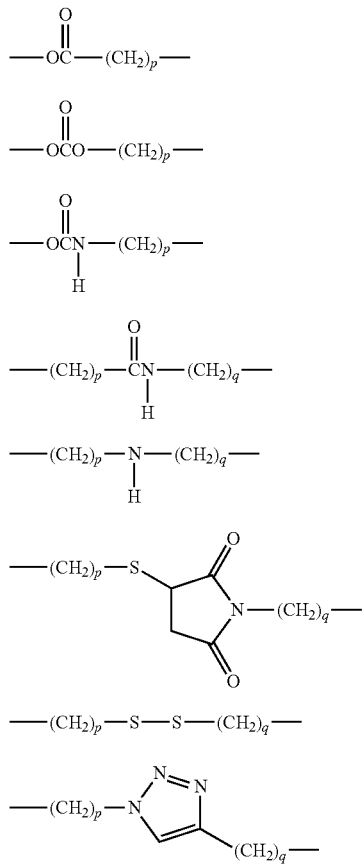

According to a preferred embodiment of the invention, prior to linking the compound of formula (5) or formula (6) to an antibody, the functional group present on the antibody is converted into another functional group by a chemical reaction, an enzyme reaction or the like, and then the functional group converted is reacted with $X^2$ of formula (5) or formula (6), thereby synthesizing the antibody-drug conjugate of formula (1) or formula (2). Preferred examples of the functional group of the antibody after the conversion include groups wherein the linkage formed by the reaction between the functional group and $X^2$ is an ether bond, an ester bond, a carbonate bond, a urethane bond, an amide bond, a thioether bond, a disulfide bond, a 1H-1,2,3-triazole-1,4-diyl group, a secondary amino group, an aliphatic hydrocarbon group containing any of these bonds and groups, a single bond or an aliphatic hydrocarbon group included in $Z^1$ or $Z^2$ of formula (1) or formula (2), and specifically include a halogen atom, an active ester, an active carbonate, an aldehyde group, an amino group, a hydroxyl group, a carboxyl group, a thiol group, an alkynyl group and an azide group.

According to another preferred embodiment of the invention, the functional group present on the antibody is reacted with one of the reactive functional groups of a bifunctional cross-linker, and the other reactive functional group of the cross linker is reacted with $X^2$ of formula (5) or formula (6), thereby synthesizing the antibody-drug conjugate of formula (1) or formula (2). Specific examples of the cross-linker can be found in a large number of general books and described, for example, in "Hermanson, G T. Bioconjugate Techniques, 2nd ed.; Academic Press: San Diego, Calif., 2008". Preferred examples of the reactive functional group of the cross linker include groups wherein the linkages formed by the reactions between the functional group and the antibody and between the reactive functional group and $X^2$ are an ether bond, an ester bond, a carbonate bond, a urethane bond, an amide bond, a thioether bond, a disulfide bond, a 1H-1,2,3-triazole-1,4-diyl group, a secondary amino group, an aliphatic hydrocarbon group containing any of these bonds and groups, a single bond or an aliphatic hydrocarbon group included in $Z^1$ or $Z^2$ of formula (1) or formula (2), and specifically include a halogen atom, an active ester, an active carbonate, an aldehyde group, an amino group, a hydroxyl group, a carboxyl group, a thiol group, a maleimide group, an alkynyl group and an azide group.

According to a preferred embodiment of the invention, the compound of formula (3) or formula (4) can be synthesized by linking a cyclic benzylidene acetal linker compound represented by formula (14) to an antibody. Moreover, the compound of formula (5) or formula (6) can be synthesized by linking the linker compound of formula (14) with a drug.

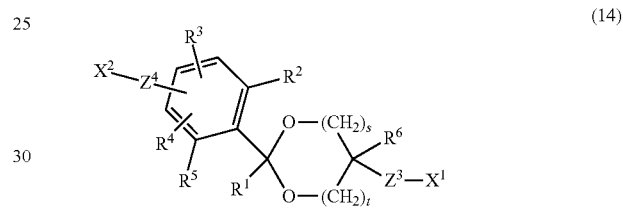

(14)

In formula (14), $X^1$ and $X^2$, which may be the same or different, are each independently a reactive functional group capable of linking to an antibody or a drug by a covalent bond, and $Z^3$ and $Z^4$ are each independently a selected divalent spacer.

$X^1$ or $X^2$ in formula (14) is not particularly limited as far as it is a reactive functional group which reacts with a functional group present on the antibody or drug to be linked to form a covalent bond. Specific examples of the reactive functional group are described in the references cited above.

Preferred examples of each of $X^1$ and $X^2$ include an active ester group, an active carbonate group, an aldehyde group, an isocyanate group, an isothiocyanate group, an epoxy group, a maleimide group, a vinyl sulfone group, an acryl group, a sulfonyloxy group, a carboxyl group, a thiol group, a dithiopyridyl group, an α-haloacetyl group, an alkynyl group, an allyl group, a vinyl group, an amino group, an oxyamino group, a hydrazide group, an azide group, a hydroxyl group, a dibenzocyclooctyne group and a bicyclo[6.1.0]nonyne group. In a more specific embodiment, the functional group capable of forming a covalent bond upon a reaction with an amino group of the reaction partner is an active ester group, an active carbonate group, an aldehyde group, an isocyanate group, an isothiocyanate group, an epoxy group, a maleimide group, a vinyl sulfone group, an acryl group, a sulfonyloxy group or a carboxyl group, the functional group capable of forming a covalent bond upon a reaction with a thiol group of the reaction partner is an active ester group, an active carbonate group, an aldehyde group, an isocyanate group, an isothiocyanate group, an epoxy group, a maleimide group, a vinyl sulfone group, an acryl group, a sulfonyloxy group, a carboxyl group, a thiol group, a dithiopyridyl group, an α-haloacetyl group, an alkynyl group, an allyl group or a vinyl group, the functional group capable of forming a covalent bond upon a reaction with an aldehyde group or a carboxyl group of the reaction partner is a thiol group, an amino group, an oxyamino group or a hydrazide group, the functional group capable of forming a covalent bond upon a reaction with an alkynyl group of the reaction partner is a thiol group or an azide group, the functional group capable of forming a covalent bond upon a reaction with an azide group of the reaction partner is an alkynyl group, a dibenzocyclooctyne group or a bicyclo[6.1.0]nonyne group, and the functional group capable of forming a covalent bond upon a reaction with a halogenated alkyl group, an alkyl sulfonic acid ester or an aryl sulfonic acid ester of the reaction partner is a hydroxyl group, a thiol group or an amino group.

In a preferred embodiment of the aspect, each of $X^1$ and $X^2$ is a group represented by group (I), group (II), group (III), group (IV), group (V) or group (VI).

Group (I): Functional group capable of forming a covalent bond upon a reaction with an amino group of the reaction partner
(a), (b), (c), (d), (e) and (f) shown below:

Group (II): Functional group capable of forming a covalent bond upon a reaction with a thiol group of the reaction partner
(a), (b), (c), (d), (e), (f), (g), (h), (i) and (j) shown below:

Group (III): Functional group capable of forming a covalent bond upon a reaction with an aldehyde group or a carboxyl group of the reaction partner
(g), (k), (l) and (m) shown below:

Group (IV): Functional group capable of forming a covalent bond upon a reaction with an alkynyl group of the reaction partner
(g), (k), (l), (m) and (n) shown below:

Group (V): Functional group each capable of forming a covalent bond upon a reaction with an azide group of the reaction partner
(j), (p) and (q) shown below:

Group (VI): Functional group each capable of forming a covalent bond upon a reaction with a halogenated alkyl group, an alkyl sulfonic acid ester or an aryl sulfonic acid ester of the reaction partner
(o), (g) and (k) shown below:

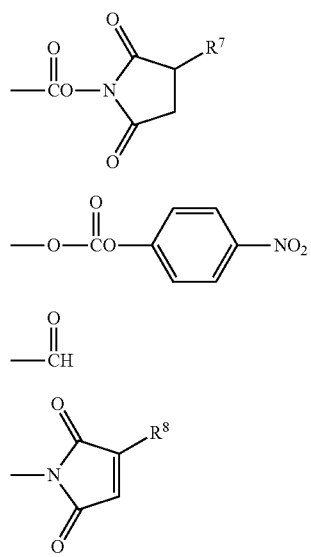

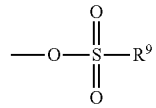 (e)

 (f)

 (g)

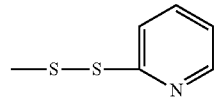 (h)

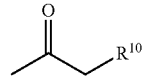 (i)

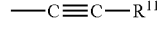 (j)

 (k)

 (l)

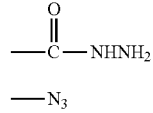 (m)

 (n)

 (o)

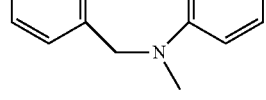 (p)

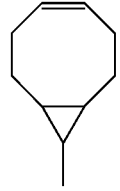 (q)

In the formulae above, $R^7$ is a hydrogen atom or a sulfo group, specific examples of the sulfo group include sodium sulfonate and potassium sulfonate, and $R^7$ is preferably a hydrogen atom. $R^8$ and $R^{11}$ are each a hydrogen atom or a hydrocarbon group having from 1 to 5 carbon atoms, and specific examples of the hydrocarbon group include a methyl group, an ethyl group, a propyl group, an isopropyl group, a butyl group, a tert-butyl group and a pentyl group. $R^9$ is a hydrocarbon group having from 1 to 10 carbon atoms which may contain a halogen atom, specific examples of the hydrocarbon group include a methyl group, an ethyl group, a propyl group, an isopropyl group, a butyl group, a tert-butyl group, a pentyl group, an isopentyl group, a hexyl group, a benzyl group, a 4-methylphenyl group, a trifluoromethyl group, a 2,2,2-trifluoroethyl group, a 4-(trifluoromethoxy)phenyl group, a vinyl group, a chloroethyl group, a bromoethyl group and an iodoethyl group, and $R^9$ is preferably a methyl group, a vinyl group, a 4-methylphenyl group or a 2,2,2-trifluoroethyl group. $R^{10}$ is a halogen atom selected from the group consisting of a chlorine atom, a bromine atom and an iodine atom.

$X^1$ and $X^2$ in formula (14) may be the same or different. As to preferred examples of the combination of $X^1$ and $X^2$ which are different from each other, when $X^1$ is an active ester group or an active carbonate group, $X^2$ is a group selected from a maleimide group, a vinyl sulfone group, an α-haloacetyl group, an alkynyl group and an azide group; when $X^1$ is an aldehyde group, $X^2$ is a group selected from a maleimide group, a vinyl sulfone group, an alkynyl group and an azide group; when $X^1$ is a maleimide group, a vinyl sulfone group or an α-haloacetyl group, $X^2$ is a group selected from an active ester group, an active carbonate group, an alkynyl group and an azide group; when $X^1$ is an alkynyl group or an azide group, $X^2$ is a group selected from a maleimide group, a vinyl sulfone group, an α-haloacetyl group, an active ester group, an active carbonate group, an amino group, an oxyamino group and a hydroxyl group; when $X^1$ is an amino group or an oxyamino group, $X^2$ is an alkynyl group, an azide group, a thiol group, a hydroxyl group or a carboxyl group; and when $X^1$ is a thiol group or a hydroxyl group, $X^2$ is a group selected from an amino group, an oxyamino group, an azide group and a carboxyl group. More preferably, when $X^1$ is an active ester or an active carbonate group, $X^2$ is a group selected from a maleimide group, an α-haloacetyl group, an alkynyl group and an azide group; when $X^1$ is an aldehyde group, $X^2$ is a group selected from a maleimide group, an α-haloacetyl group, an alkynyl group and an azide group; when $X^1$ is a maleimide group or an α-haloacetyl group, $X^2$ is a group selected from an active ester group, an active carbonate group, an alkynyl group and an azide group; when $X^1$ is an alkynyl group or an azide group, $X^2$ is a group selected from a maleimide group, an α-haloacetyl group, an active ester group, an active carbonate group, an amino group, an oxyamino group and a hydroxyl group; when $X^1$ is an amino group or an oxyamino group, $X^2$ is an alkynyl group, an azide group, a hydroxyl group or a thiol group; and when $X^1$ is a thiol group or a hydroxyl group, $X^2$ is a group selected from an amino group, an oxyamino group and an azide group.

$Z^3$ in formula (14) is a divalent spacer between the acetal group of the cyclic benzylidene acetal and $X^1$, and $Z^4$ in formula (14) is a divalent spacer between the benzene ring and $X^2$. These are composed of covalent bonds, are not particularly limited as far as they are more stable to acid hydrolysis than the cyclic benzylidene acetal group, and are preferably an ether bond, an ester bond, a carbonate bond, a urethane bond, an amide bond, a thioether bond, a disulfide bond, a 1H-1,2,3-triazole-1,4-diyl group, a secondary amino group, an aliphatic hydrocarbon group containing any of these bonds and groups, a single bond or an aliphatic hydrocarbon group. The number of carbon atoms of the aliphatic hydrocarbon group is preferably from 1 to 24. By way of illustration and without limitation, preferred examples of the aliphatic hydrocarbon group include structures such as (z1). Preferred examples of the aliphatic hydrocarbon group having an ether bond include structures such as (z2) or (z3). Preferred examples of the aliphatic hydrocarbon group having an ester bond include structures such as (z4). Preferred examples of the aliphatic hydrocarbon group having a carbonate bond include structures such as (z5). Preferred examples of the aliphatic hydrocarbon group having a urethane bond include structures such as (z6). Preferred examples of the aliphatic hydrocarbon group having an amide bond include structures such as (z7). Preferred examples of the aliphatic hydrocarbon group having a secondary amino group include structures such as (z8). Preferred examples of the aliphatic hydrocarbon group having a thioether bond include structures such as (z9). Preferred examples of the aliphatic hydrocarbon group having a disulfide bond include structures such as (z10). Preferred examples of the aliphatic hydrocarbon group having a 1H-1,2,3-triazole-1,4-diyl group include structures such as (z11). In a preferred embodiment, p and q are each independently an integer of 1 to 12. However, in the case where at least one of $Z^3$ and $Z^4$ is an ether bond, an ester bond, a carbonate bond, a urethane bond, an amide bond, a thioether bond, a disulfide bond, a 1H-1,2,3-triazole-1,4-diyl group, a secondary amino group or an aliphatic hydrocarbon group containing any of these bonds and groups and a plurality of identical structural units are bound, a number of the structural units described above is 2 or less.

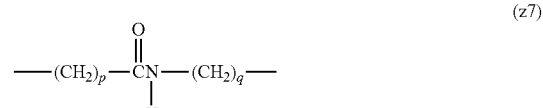
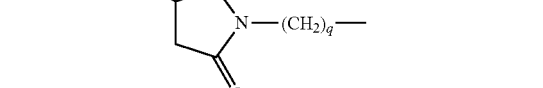

The bond generated by a coupling reaction between the linker compound of formula (14) and the antibody or the drug is determined by a combination of the functional groups used in the reaction, and is an ether bond, an ester bond, a carbonate bond, a urethane bond, an amide bond, a thioether bond, a disulfide bond, a 1H-1,2,3-triazole-1,4-diyl group, a secondary amino group, an aliphatic hydrocarbon group containing any of these bonds and groups, a single bond or an aliphatic hydrocarbon group included in $Z^1$ or $Z^2$ of formula (3) or formula (4) and formula (5) or formula (6), and specifically includes a halogen atom, an active ester, an active carbonate, an aldehyde group, an amino group, a hydroxyl group, a carboxyl group, a thiol group, a maleimide group, an alkynyl group and an azide group. The compound of formula (3) or formula (4) and the compound of formula (5) or formula (6) synthesized are subjected to chemical conversion of the terminal functional group, if desired. As the reaction for use in the functional group conversion, conventionally known methods can be used, but the conditions which do not decompose the cyclic benzylidene acetal group and the bonds included in the divalent spacers of $Z^1$, $Z^2$, $Z^3$ and $Z^4$ must be properly selected.

According to a preferred embodiment of the invention, prior to linking an antibody or a drug to the linker compound of formula (14), the functional group present on the antibody or drug is converted into another functional group by a chemical reaction, an enzyme reaction or the like, and then the functional group converted is reacted with $X^1$ or $X^2$ of formula (14), thereby synthesizing the compound of formula (3) or formula (4) or the compound of formula (5) or formula (6). Preferred examples of the functional group of the antibody or drug after the conversion include groups wherein the linkage formed by the reaction between the functional group and $X^1$ or $X^2$ is an ether bond, an ester bond, a carbonate bond, a urethane bond, an amide bond, a thioether bond, a disulfide bond, a 1H-1,2,3-triazole-1,4-diyl group, a secondary amino group, an aliphatic hydrocarbon group containing any of these bonds and groups, a single bond or an aliphatic hydrocarbon group included in $Z^1$ or $Z^2$ of formula (3) or formula (4) or formula (5) or formula (6), and specifically include a halogen atom, an active ester, an active carbonate, an aldehyde group, an amino group, a hydroxyl group, a carboxyl group, a thiol group, an alkynyl group and an azide group.

According to another preferred embodiment of the invention, the functional group present on the antibody or drug is reacted with one of the reactive functional groups of a bifunctional cross-linker, and the other reactive functional group of the cross linker is reacted with $X^1$ or $X^2$ of formula (14), thereby synthesizing the compound of formula (3) or formula (4) or the compound of formula (5) or formula (6). Specific examples of the cross-linker are described in the references cited above. Preferred examples of the reactive functional group of the cross linker include groups wherein the bonds formed by the reactions between the functional group and the antibody or drug and between the reactive functional group and $X^1$ or $X^2$ are an ether bond, an ester bond, a carbonate bond, a urethane bond, an amide bond, a thioether bond, a disulfide bond, a 1H-1,2,3-triazole-1,4-diyl group, a secondary amino group, an aliphatic hydrocarbon group containing any of these bonds and groups, a single bond or an aliphatic hydrocarbon group included in $Z^1$ or $Z^2$ of formula (3) or formula (4) or formula (5) or formula (6), and specifically include a halogen atom, an active ester, an active carbonate, an aldehyde group, an amino group, a hydroxyl group, a carboxyl group, a thiol group, a maleimide group, an alkynyl group and an azide group.

A typical example for synthesizing the cyclic benzylidene acetal linker compound is described below, but the invention should not be construed as being limited thereto.

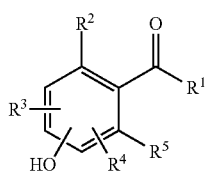

(15)

(in the formula, $R^1$ is a hydrogen atom or a hydrocarbon group; and $R^2$, $R^3$, $R^4$ and $R^5$ are each independently an electron-withdrawing or electron-donating substituent or a hydrogen atom.)

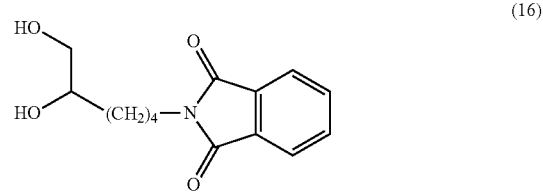

(16)

A carbonyl compound of formula (15) having a hydroxy group which is a chemically reactive functional group is allowed to react with a 1,2-diol derivative of formula (16) having a phthalimide group in which an amino group is protected with a phthaloyl group in an aprotic solvent, for example, toluene, benzene, xylene, acetonitrile, ethyl acetate, diethyl ether, tert-butyl methyl ether, tetrahydrofuran, chloroform, dichloromethane, dimethyl sulfoxide, dimethylformamide or dimethylacetamide or with no solvent in the presence of an acid catalyst to obtain a compound of formula (17) shown below having a cyclic benzylidene acetal group. The resulting compound may be purified by extraction, recrystallization, adsorbent treatment, column chromatography or the like. In place of the carbonyl compound, it is possible to use a corresponding acetal derivative of a lower alcohol. The lower alcohol is preferably an alcohol having from 1 to 5 carbon atoms, and more preferably methanol or ethanol. The acid catalyst may be either an organic acid or an inorganic acid and is not particularly limited, and specific examples thereof include p-toluenesulfonic acid, pyridinium p-toluenesulfonate, methanesulfonic acid, 10-camphorsulfonic acid, hydrogen chloride, iodine, ammonium chloride, oxalic acid, boron trifluoride-diethyl ether complex and the like.

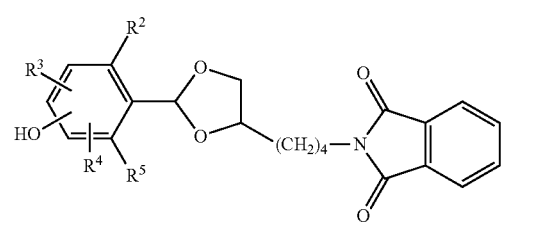

(17)

The "protective group" as referred to herein is a component which prevents or blocks a reaction of a specific chemically reactive functional group in a molecule under certain reaction conditions. The protective group varies depending on the kind of the chemically reactive functional group to be protected, the conditions to be used and the presence of other functional group or protective group in the molecule. Specific examples of the protective group can be found in a large number of general books and are described, for example, in "Wuts, P. G M.; Greene, T. W., Protective Groups in Organic Synthesis, 4th ed.; Wiley-Interscience: New York, 2007". Moreover, the functional group protected by the protective group can be reproduce the original functional group by deprotection using reaction conditions suitable for each of the protective groups, that is, causing a chemical reaction. Therefore, in the specification, a functional group which is protected by a protective group and is capable of being deprotected by various reactions is included in the "chemically reactive functional group". The typical deprotection conditions of the protective group are described in the reference cited above.

As the chemically reactive functional group in the compound of formula (15), a functional group other than the hydroxyl group can also be used. Specific examples thereof include a hydroxyalkyl group, an amino group, an aminoalkyl group, a carboxyl group and a carboxyalkyl group. Also, the functional group described above may be protected by a protective group which is stable in the acidic conditions of the acetalization reaction and can be deprotected under reaction conditions other than catalytic reduction by which the cyclic benzylidene acetal group is decomposed. As to preferred combinations of the functional group to be protected and the protective group, when the functional group to be protected is a hydroxyl group or a hydroxyalkyl group, for example, a silyl protective group and an acyl protective group are exemplified, and specific examples thereof include a tert-butyldiphenylsilyl group, a tert-butyldimethylsilyl group, a triisopropylsilyl group, an acetyl group and a pivaloyl group. When the functional group to be protected is an amino group or an aminoalkyl group, for example, an acyl protective group and a carbamate protective group are exemplified, and specific examples thereof include a trifluoroacetyl group, a 9-fluorenylmethyloxycarbonyl group and a 2-(trimethylsilyl)ethyloxycarbonyl group. When the functional group to be protected is a carboxyl group or a carboxyalkyl group, for example, an alkyl ester protective group and a silyl ester protective group are exemplified, and specific examples thereof include a methyl group, a 9-fluorenylmethyl group and a tert-butyldimethylsilyl group. The kinds and the typical deprotection conditions of the specific protective groups are described in the reference cited above, and the reaction conditions suitable for each of the protective groups are selected and the deprotection can be performed at a proper timing in a sequence of the synthesis steps of the cyclic benzylidene acetal linker compound.

Moreover, as the chemically reactive functional group excepting the 1,2-diol moiety in the compound of formula (16), a functional group other than the phthalimide group can also be used. In the case where the chemically reactive functional group is a functional group which is protected by a protective group, it is necessary that the protective group is stable in the acidic conditions of the acetalization reaction and can be deprotected under reaction conditions other than catalytic reduction by which the benzylidene acetal group is decomposed. As to preferred combinations of the functional group to be protected and the protective group, when the functional group to be protected is an amino group, for example, an acyl protective group and a carbamate protective group are exemplified, and specific examples thereof include a trifluoroacetyl group, a 9-fluorenylmethyloxycarbonyl group and a 2-(trimethylsilyl)ethyloxycarbonyl group. When the functional group to be protected is a hydroxyl group, for example, a silyl protective group and an acyl protective group are exemplified, and specific examples thereof include a tert-butyldiphenylsilyl group, a tert-butyldimethylsilyl group, a triisopropylsilyl group, an acetyl group and a pivaloyl group. When the functional group to be protected is a carboxyl group, for example, an alkyl ester protective group and a silyl ester protective group are exemplified, and specific examples thereof include a methyl group, a 9-fluorenylmethyl group and a tert-butyldimethylsilyl group. When the functional group to be protected is a sulfanyl group, for example, a thioether protective group, a thiocarbonate protective group and a disulfide protective group are exemplified, and specific examples thereof include an S-2,4-dinitrophenyl group, an S-9-fluorenylmethyloxycarbonyl group and an S-tert-butyldisulfide group. The typical deprotection conditions of the protective group are described in the reference cited above, and the reaction conditions suitable for each of the protective groups are selected. However, in the case where the chemically reactive functional group is a functional group which does not inhibit the acetalization reaction even when it is not protected by a protective group, it is not necessary to use a protective group.

Diethylene glycol is allowed to react with methanesulfonyl chloride in an aprotic solvent, for example, toluene, benzene, xylene, acetonitrile, ethyl acetate, diethyl ether, tert-butyl methyl ether, tetrahydrofuran, chloroform, dichloromethane, dimethyl sulfoxide, dimethylformamide or dimethylacetamide or with no solvent in the presence of an organic base, for example, triethylamine, N-methylmorpholine, pyridine or 4-dimethylaminopyridine or an inorganic base, for example, sodium carbonate, sodium hydrogen carbonate, sodium acetate or potassium carbonate to obtain a compound of formula (18). The organic base and inorganic base may not be used. The use ratio of the organic base or the inorganic base is not particularly limited, and is preferably 0.5 molar equivalent or less to the hydroxyl group of the diethylene glycol. The organic base may also be used as a solvent. The compound obtained may be purified by a purification means, for example, extraction, recrystallization, adsorbent treatment, reprecipitation, column chromatography or supercritical extraction.

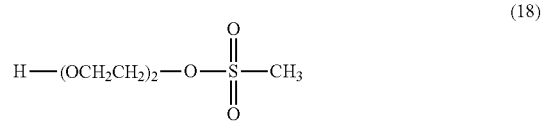

(18)

The compound of formula (17) and the compound of formula (18) are subjected to a coupling reaction in an aprotic solvent, for example, toluene, benzene, xylene, acetonitrile, ethyl acetate, diethyl ether, tert-butyl methyl ether, tetrahydrofuran, chloroform, dichloromethane, dimethyl sulfoxide, dimethylformamide or dimethylacetamide or with no solvent in the presence of an organic base, for example, triethylamine, N-methylmorpholine, potassium tert-butoxide or sodium hexamethyldisilazane or an inorganic base, for example, potassium carbonate, potassium hydroxide or sodium hydride to obtain a compound of formula (19). The use ratio of the organic base or the inorganic base is not particularly limited, and is preferably equimolar or more to the chemically reactive functional group of the compound of formula (18). The organic base may also be used as a solvent. The compound obtained may be purified by the purification means described above.

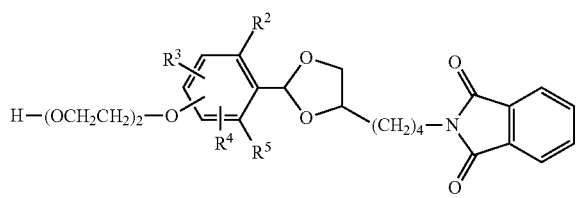

(19)

The compound of formula (19) is treated by using a basic organic compound, for example, ethylenediamine, methylhydrazine or methylamine or a basic inorganic compound, for example, hydrazine, hydroxylamine or sodium hydroxide in a protic solvent, for example, water, methanol or ethanol, in an aprotic solvent, for example, acetonitrile, tetrahydrofuran, dimethyl sulfoxide, dimethylformamide or dimethylacetamide or with no solvent to obtain a compound of formula (20) in which the phthalimide group is deprotected and converted into an amino group. The use ratio of the basic compound is not particularly limited, and is preferably equimolar or more to the chemically reactive functional group of the compound of formula (19). The basic compound may also be used as a solvent. The compound obtained may be purified by the purification means described above.

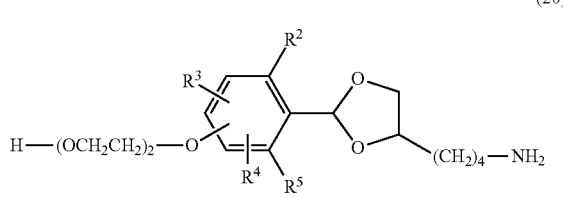

(20)

The compound of formula (20) is allowed to react with N-succinimidyl 3-maleimidopropionate in an aprotic solvent, for example, toluene, benzene, xylene, acetonitrile, ethyl acetate, diethyl ether, tert-butyl methyl ether, tetrahydrofuran, chloroform, dichloromethane, dimethyl sulfoxide, dimethylformamide or dimethylacetamide or with no solvent in the presence of an organic base, for example, triethylamine, N-methylmorpholine, pyridine or 4-dimethylaminopyridine or an inorganic base, for example, sodium carbonate, sodium hydrogen carbonate, sodium acetate or potassium carbonate to obtain a compound of formula (21) in which a maleimide group is introduced into the terminal. The organic base and inorganic base may not be used. The use ratio of the organic base or the inorganic base is not particularly limited, and is preferably equimolar or more to the chemically reactive functional group of the compound of formula (20). The organic base may also be used as a solvent. The compound obtained may be purified by the purification means described above.

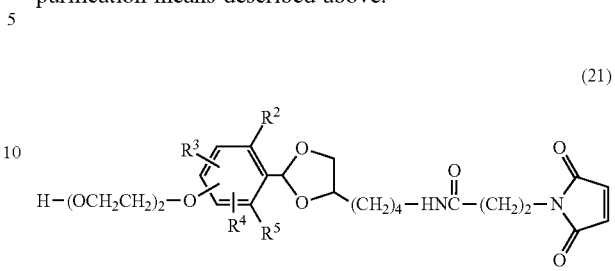

(21)

The compound of formula (21) is allowed to react with N,N'-disuccinimidyl carbonate in an aprotic solvent, for example, toluene, benzene, xylene, acetonitrile, ethyl acetate, diethyl ether, tert-butyl methyl ether, tetrahydrofuran, chloroform, dichloromethane, dimethyl sulfoxide, dimethylformamide or dimethylacetamide or with no solvent in the presence of an organic base, for example, triethylamine, N-methylmorpholine, pyridine or 4-dimethylaminopyridine or an inorganic base, for example, sodium carbonate, sodium hydrogen carbonate, sodium acetate or potassium carbonate to obtain a compound of formula (22) in which a N-hydroxysuccinimidyl carbonate group is introduced into the terminal. The organic base and inorganic base may not be used. The use ratio of the organic base or the inorganic base is not particularly limited, and is preferably equimolar or more to the chemically reactive functional group of the compound of formula (21). The organic base may also be used as a solvent. The compound obtained may be purified by the purification means described above.

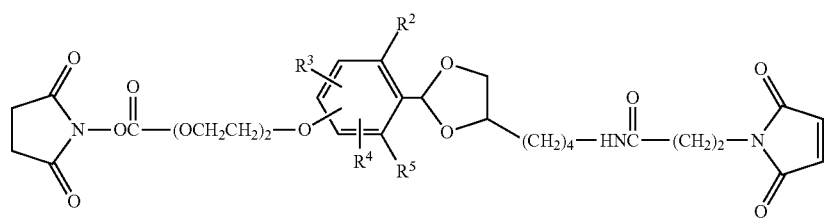

(22)

EXAMPLES

The invention will be described more specifically with reference to the examples, but the invention should not be construed as being limited thereto.

In $^1$H-NMR analysis, JNM-ECP400 or JNM-ECA600 produced by JEOL DATUM Ltd. was used. For the measurement, a tube of 5 mm φ was used, and tetramethylsilane (TMS) was used as an internal standard substance in the case where a deuterated solvent was $CDCl_3$, $CD_3CN$ or $CD_3OD$, or HDO was used as a standard in the case of $D_2O$.

Example 1

Into a 200 mL three-necked flask equipped with a thermometer, a nitrogen inlet tube, a stirrer, a Dean-stark tube and a condenser tube were charged 1,2,6-hexanetriol (30.0 g, 0.224 mol), acetone dimethyl acetal (25.6 g, 0.246 mol) and p-toluenesulfonic acid monohydrate (0.426 g, 2.24 mmol), and the reaction was performed at 80° C. for 3 hours while distilling off methanol. Triethylamine (0.453 g, 4.48 mmol) was added thereto and the mixture was stirred for a while, diluted with ethyl acetate, and washed with an aqueous 20% by weight sodium chloride solution. The organic layer was dried over anhydrous sodium sulfate, and after filtration, the solvent was distilled off under a reduced pressure. The residue was purified by silica gel chromatography to obtain a compound of formula (23).

$^1$H-NMR (CDCl$_3$, internal standard TMS); δ (ppm): 1.35 (3H, s, —C$\underline{H}_3$), 1.41 (3H, s, —C$\underline{H}_3$), 1.49-1.67 (6H, m, >CHC$\underline{H}_2$C$\underline{H}_2$C$\underline{H}_2$—), 2.07 (1H, brs, —O$\underline{H}$), 3.51 (1H, t, —OC$\underline{H}_2$CH<), 3.64 (2H, t, —C$\underline{H}_2$OH), 4.04 (1H, dd, —OCH$_2$CH<), 4.07-4.10 (1H, m, —OCH$_2$C$\underline{H}$<)

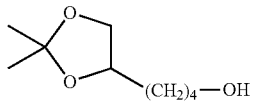

(23)

Example 2

Into a 500 mL four-necked flask equipped with a thermometer, a nitrogen inlet tube, a stirrer and a condenser tube were charged the compound of formula (23) (20.0 g, 0.115 mol), triethylamine (23.3 g, 0.230 mol) and toluene (200 g) and the mixture was cooled to 10° C. or less. While continuing the cooling, methanesulfonyl chloride (19.8 g, 0.173 mol) prepared in a dropping funnel was gradually added dropwise thereto. After the completion of the dropwise addition, the reaction was performed at 20° C. for 2 hours. Ethanol (7.97 g, 0.173 mol) was added and the mixture was stirred for some time and then filtered. The organic layer was washed with ion-exchanged water, dried over anhydrous sodium sulfate, and after filtration, the solvent was distilled off under a reduced pressure to obtain a compound of formula (24).

$^1$H-NMR (CDCl$_3$, internal standard TMS); δ (ppm): 1.35 (3H, s, —C$\underline{H}_3$), 1.40 (3H, s, —C$\underline{H}_3$), 1.44-1.83 (6H, m, >CHC$\underline{H}_2$C$\underline{H}_2$C$\underline{H}_2$—), 3.01 (3H, s, —OSO$_2$C$\underline{H}_3$), 3.51 (1H, t, —OC$\underline{H}_2$CH<), 4.03-4.11 (2H, m, —OCH$_2$CH<, —OCH$_2$C$\underline{H}$<), 4.24 (2H, t, —C$\underline{H}_2$OSO$_2$CH$_3$)

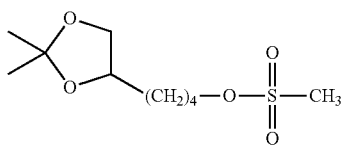

(24)

Example 3

Into a 500 mL four-necked flask equipped with a thermometer, a nitrogen inlet tube, a stirrer and a condenser tube were charged the compound of formula (24) (20.0 g, 79.3 mmol), potassium phthalimide (17.6 g, 95.2 mmol) and dehydrated dimethylformamide (200 g), and the reaction was performed at 60° C. for 2 hours. The mixture was cooled to 10° C. or less, ion-exchanged water (400 g) was added thereto and after stirring for a while, the mixture was extracted with a mixed solution of ethyl acetate/hexane (60/40 in v/v). The organic layer was washed with an aqueous 0.2% by weight potassium carbonate solution and dried over anhydrous sodium sulfate. After filtration, the solvent was distilled off under a reduced pressure to obtain a compound of formula (25).

$^1$H-NMR (CDCl$_3$, internal standard TMS); δ (ppm): 1.34 (3H, s, —C$\underline{H}_3$), 1.39 (3H, s, —C$\underline{H}_3$), 1.44-1.75 (6H, m, >CHC$\underline{H}_2$C$\underline{H}_2$C$\underline{H}_2$—), 3.50 (1H, t, —OC$\underline{H}_2$CH<), 3.69 (2H, t, —C$\underline{H}_2$-phthalimide), 4.01-4.09 (2H, m, —OC$\underline{H}_2$CH<, —OCH$_2$C$\underline{H}$<), 7.71-7.85 (4H, m, -phthalimide)

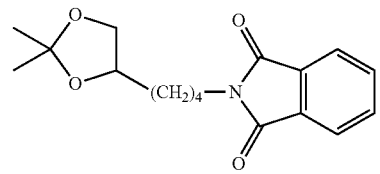

(25)

Example 4

Into a 1 L four-necked flask equipped with a thermometer, a nitrogen inlet tube, a stirrer and a condenser tube were charged the compound of formula (25) (15.2 g, 50.0 mmol), p-toluenesulfonic acid monohydrate (951 mg, 5.00 mmol) and methanol (500 mL), and the reaction was performed at room temperature for 4 hours. Triethylamine (1.01 g, 10.0 mmol) was added thereto and after stirring for a while, the solvent was distilled off under a reduced pressure. The residue was dissolved in chloroform, the solution was washed with ion-exchanged water, and the organic layer was dried over anhydrous sodium sulfate. After filtration, the solvent was distilled off under a reduced pressure to obtain a compound of formula (26).

$^1$H-NMR (CD$_3$CN, internal standard TMS); δ (ppm): 1.24-1.61 (6H, m, >CHC$\underline{H}_2$C$\underline{H}_2$C$\underline{H}_2$—), 2.69 (1H, t, —O$\underline{H}$), 2.75 (1H, d, —O$\underline{H}$), 3.17-3.21 (1H, m, —OC$\underline{H}_2$CH<), 3.31-3.37 (1H, m, —OC$\underline{H}_2$CH<), 3.39-3.43 (1H, m, —OCH$_2$C$\underline{H}$<), 3.54 (2H, t, —C$\underline{H}_2$-phthalimide), 7.67-7.75 (4H, m, -phthalimide)

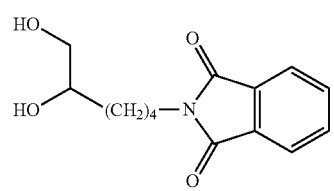

(26)

Example 5

Into a 300 mL three-necked flask equipped with a thermometer, a nitrogen inlet tube, a stirrer, a Dean-stark tube and a condenser tube were charged the compound of formula

(26) (3.87 g, 14.7 mmol), 4-hydroxybenzaldehyde (1.20 g, 9.83 mmol), pyridinium p-toluenesulfonate (247 mg, 0.983 mmol) and toluene (180 g), and the reaction was performed for 4 hours while removing by-produced water by azeotropic distillation with toluene. Triethylamine (199 mg, 1.97 mmol) was added thereto and after stirring for a while, the solvent was distilled off under a reduced pressure. The residue was dissolved in chloroform, the solution was washed in order with an aqueous 20% by weight sodium chloride solution and ion-exchanged water, and the organic layer was dried over anhydrous sodium sulfate. After filtration, the solvent was distilled off under a reduced pressure to obtain a compound of formula (27).

$^1$H-NMR (CDCl$_3$, internal standard TMS); δ (ppm): 1.41-1.80 (6H, m, >CHC$\underline{H}_2$C$\underline{H}_2$C$\underline{H}_2$—), 3.57-4.26 (5H, m, —OC$\underline{H}_2$C$\underline{H}$<, —C$\underline{H}_2$-phthalimide), 5.71 (0.6H, s, >C$\underline{H}$—), 5.82 (0.4H, s, >C$\underline{H}$—), 6.79-6.82 (2H, m, arom.$\underline{H}$), 7.31-7.35 (2H, m, arom.$\underline{H}$), 7.70-7.86 (4H, m, -phthalimide)

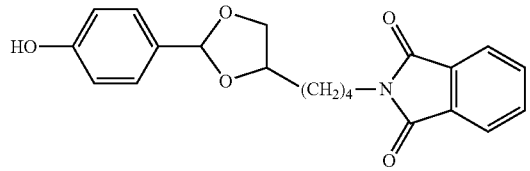

(27)

Example 6

Into a 500 mL three-necked flask equipped with a thermometer, a nitrogen inlet tube, a stirrer, a Dean-stark tube and a condenser tube were charged diethylene glycol (2.12 g, 20.0 mmol) and toluene (250 g), and water was removed by azeotropic distillation with toluene. After cooling to 40° C., triethylamine (1.21 g, 12.0 mmol) was charged and methane sulfonyl chloride (1.15 g, 10.0 mmol) prepared in a dropping funnel was gradually added dropwise thereto. After the completion of the dropwise addition, the reaction was performed at 40° C. for 3 hours. Ethanol (0.46 g, 10.0 mmol) was added thereto and the mixture was stirred for a while, filtered, and the solvent was distilled off under a reduced pressure. The residue was purified by silica gel column chromatography to obtain a compound of formula (29).

$^1$H-NMR (CDCl$_3$, internal standard TMS); δ (ppm): 3.08 (3H, s, —OSO$_2$C$\underline{H}_3$), 3.52-3.85 (6H, m, —OC$\underline{H}_2$C$\underline{H}_2$—OC$\underline{H}_2$—), 4.37-4.39 (2H, m, —C$\underline{H}_2$OSO$_2$CH$_3$)

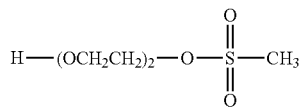

(29)

Example 7

Into a 100 mL three-necked flask equipped with a thermometer, a nitrogen inlet tube, a stirrer and a condenser tube were charged the compound of formula (29) (184 mg, 1.00 mmol), the compound of formula (27) (551 mg, 1.50 mmol), potassium carbonate (691 mg, 5.00 mmol) and acetonitrile (25 g), and the reaction was performed at 80° C. for 4 hours. After filtration, the solvent was distilled off under a reduced pressure. The residue was purified by silica gel column chromatography to obtain a compound of formula (30).

$^1$H-NMR (CDCl$_3$, internal standard TMS); δ (ppm): 1.40-1.81 (6H, m, >CHC$\underline{H}_2$C$\underline{H}_2$C$\underline{H}_2$—), 3.52-4.25 (13H, m, —OC$\underline{H}_2$C$\underline{H}_2$—, —OC$\underline{H}_2$C$\underline{H}$<, —C$\underline{H}_2$-phthalimide), 5.72 (0.6H, s, >C$\underline{H}$—), 5.84 (0.4H, s, >C$\underline{H}$—), 6.89-6.91 (2H, m, arom.$\underline{H}$), 7.35-7.39 (2H, m, arom.$\underline{H}$), 7.70-7.86 (4H, m, -phthalimide)

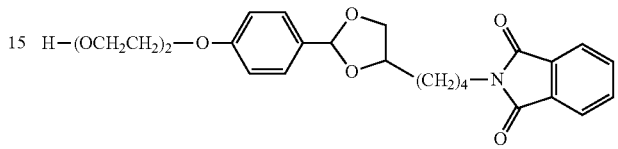

(30)

Example 8

Into a 50 mL three-necked flask equipped with a thermometer, a nitrogen inlet tube, a stirrer and a condenser tube were charged the compound of formula (30) (364 mg, 0.800 mmol), methanol (7 g) and ethylene diamine monohydrate (1.56 g, 20.0 mmol), and the reaction was performed at 40° C. for 4 hours. The mixture was diluted with an aqueous 20% by weight sodium chloride solution, extracted with dichloromethane, and the solvent was distilled off under a reduced pressure. The residue was dissolved in ethyl acetate (50 g), dried over anhydrous sodium sulfate, filtered, and the solvent was distilled off under a reduced pressure. The residue was purified by silica gel column chromatography to obtain a compound of formula (31).

$^1$H-NMR (CD$_3$OD, internal standard TMS); δ (ppm): 1.43-1.79 (6H, m, >CHC$\underline{H}_2$C$\underline{H}_2$C$\underline{H}_2$—), 2.77 (2H, t, —C$\underline{H}_2$—NH$_2$), 3.50-4.29 (11$\underline{H}$, m, —OC$\underline{H}_2$C$\underline{H}_2$—, —OC$\underline{H}_2$C$\underline{H}$<), 5.70 (0.6H, s, >C$\underline{H}$—), 5.81 (0.4H, s, >C$\underline{H}$—), 6.93-6.98 (2H, m, arom.$\underline{H}$), 7.33-7.41 (2H, m, arom.$\underline{H}$)

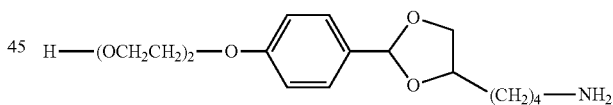

(31)

Example 9

Into a 50 mL three-necked flask equipped with a thermometer, a nitrogen inlet tube, a stirrer and a condenser tube were charged the compound of formula (31) (163 mg, 0.500 mmol) and acetonitrile (10 g), and N-succinimidyl 3-maleimidopropionate (160 mg, 0.600 mmol) was added thereto, and the reaction was performed at 25° C. for 3 hours. After filtration, the solvent was distilled off under a reduced pressure. After filtration, the solvent was distilled off under a reduced pressure. The residue was purified by silica gel column chromatography to obtain a compound of formula (32).

$^1$H-NMR (CDCl$_3$, internal standard TMS); δ (ppm): 1.40-1.81 (6H, m, >CHC$\underline{H}_2$C$\underline{H}_2$C$\underline{H}_2$—), 2.44 (2H, t, —C$\underline{H}_2$CH$_2$-maleimide), 3.27-3.37 (2H, m, —C$\underline{H}_2$NHCO—), 3.47-4.25 (13H, m, —OC$\underline{H}_2$C$\underline{H}_2$—, —OC$\underline{H}_2$C$\underline{H}$<, —CH$_2$C$\underline{H}_2$-maleimide), 5.72 (0.6$\underline{H}$, s, >C$\underline{H}$—), 5.84 (0.4H, s, >C$\underline{H}$—), 6.15 (1H, brs, —N$\underline{H}$CO—), 6.70 (2H, s, -maleimide), 6.89-6.91 (2H, m, arom.$\underline{H}$), 7.35-7.39 (2H, m, arom.$\underline{H}$)

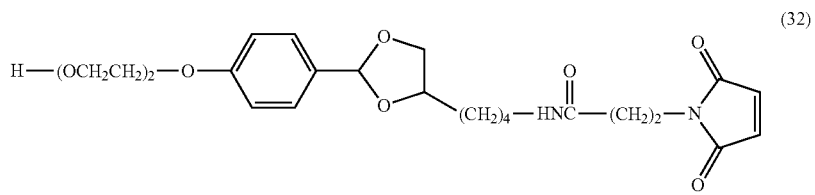

Example 10

The compound of formula (32) was allowed to react with N,N'-disuccinimidyl carbonate in dichloromethane in the presence of triethylamine to obtain a compound of formula (33).

$^1$H-NMR (CDCl$_3$, internal standard TMS); δ (ppm): 1.40-1.81 (614, m, >CHC$\underline{H}_2$C$\underline{H}_2$C$\underline{H}_2$—), 2.44 (2H, t, —C$\underline{H}_2$CH$_2$-maleimide), 2.84 (4H s, -succinimide), 3.27-3.37 (2H, m, —C$\underline{H}_2$NHCO—), 3.40-4.23 (11H, m, —OC$\underline{H}_2$C$\underline{H}_2$—OC$\underline{H}_2$—, —OC$\underline{H}_2$C$\underline{H}$<, —C$\underline{H}_2$CH$_2$-maleimide), 4.44-4.48 (2H, m, —C$\underline{H}_2$O—COO-succinimide), 5.70 (0.6H, s, >C$\underline{H}$—), 5.82 (0.4H, s, >C$\underline{H}$—), 6.15 (1H, brs, —N$\underline{H}$CO—), 6.70 (2H, s, -maleimide), 6.95-7.21 (3H, m, arom.$\underline{H}$)

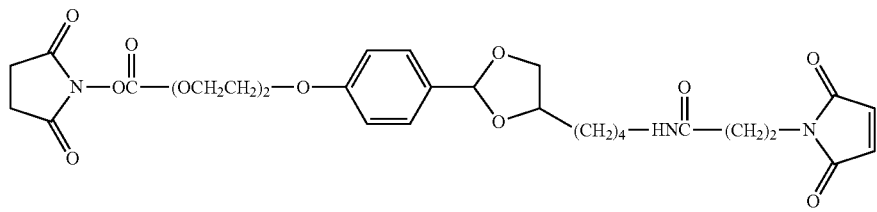

Example 11

A compound of formula (34) was obtained in the same manner as in Examples 1 to 10 using 3-fluoro-4-hydroxybenzaldehyde.

$^1$H-NMR (CDCl$_3$, internal standard TMS); δ (ppm): 1.38-1.80 (6H, m, >CHC$\underline{H}_2$C$\underline{H}_2$C$\underline{H}_2$—), 3.52-4.23 (11H, m, —OC$\underline{H}_2$C$\underline{H}_2$—, —OC$\underline{H}_2$C$\underline{H}$<, —C$\underline{H}_2$-phthalimide), 5.70 (0.6H, s, >C$\underline{H}$—), 5.82 (0.4H, s, >C$\underline{H}$—), 6.95-7.21 (3H, m, arom.$\underline{H}$), 7.70-7.86 (4H, m, -phthalimide)

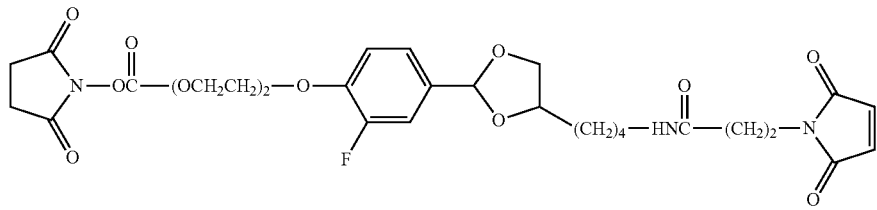

Example 12

A compound of formula (35) was obtained in the same manner as in Examples 1 to 10 using 2-bromo-5-hydroxybenzaldehyde.

$^1$H-NMR (CDCl$_3$, internal standard TMS); δ (ppm): 1.38-1.80 (6H, m, >CHC$\underline{H}_2$C$\underline{H}_2$C$\underline{H}_2$—), 3.52-4.23 (11H, m, —OC$\underline{H}_2$C$\underline{H}_2$—, —OC$\underline{H}_2$C$\underline{H}$<, —C$\underline{H}_2$-phthalimide), 5.70 (0.6H, s, >C$\underline{H}$—), 5.82 (0.4H, s, >C$\underline{H}$—), 6.95-7.21 (3H, m, arom.$\underline{H}$), 7.70-7.86 (4H, m, -phthalimide)

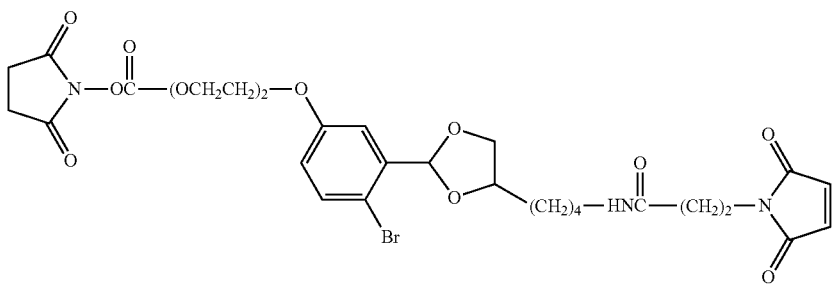

(35)

Example 13

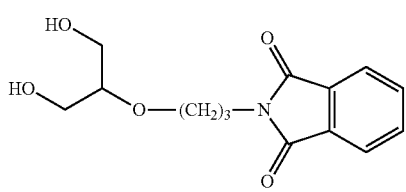

(36)

A compound of formula (36) was synthesized in a manner similar to Examples 1 to 4, and then a compound of formula (37) was obtained in the same manner as in Examples 5 to 7 using 3-fluoro-4-hydroxybenzaldehyde.

¹H-NMR (CDCl₃, internal standard TMS); δ (ppm): 1.89 (2H, m, —CH₂CH₂-phthalimide), 3.19 (1H, m, —OCH₂CH<), 3.52-4.41 (16H, m, —OCH₂CH₂—, —OCH₂CH<, —CH₂CH₂CH₂-phthalimide), 5.34 (0.8H, s, >CH—), 5.42 (0.2H, s, >CH—), 6.95-7.25 (3H, m, arom.H), 7.70-7.86 (4H, m, -phthalimide)

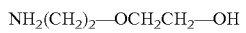

(37)

Example 14

A compound of formula (38) was obtained in the same manner as in Examples 5 to 8 using the compound of formula (36) and 2-bromo-5-hydroxybenzaldehyde.

¹H-NMR (CDCl₃, internal standard TMS); δ (ppm): 1.89 (2H, m, —CH₂CH₂-phthalimide), 3.19 (1H, m, —OCH₂CH<), 3.52-4.41 (16H, m, —OCH₂CH₂—, —OCH₂CH<, —CH₂CH₂CH₂-phthalimide), 5.61 (0.8H, s, >CH—), 5.68 (0.2H, s, >CH—), 6.78-7.40 (3H, m, arom.H), 7.70-7.86 (4H, m, -phthalimide)

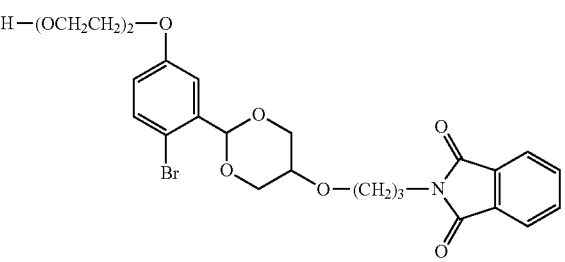

(38)

Example 15

NH₂(CH₂)₂—OCH₂CH₂—OH    (39)

A compound of formula (40) was obtained by allowing to react the compound of formula (39) with 5-azidopentanoic anhydride.

¹H-NMR (CDCl₃, internal standard TMS); δ (ppm): 1.60-1.74 (4H, m, —CH₂CH₂CH₂CH₂N₃), 2.18 (2H, t, —CH₂CH₂CH₂CH₂N₃), 3.29 (2H, t, —CH₂CH₂CH₂CH₂N₃), 3.40-3.85 (8H, m, —OCH₂CH₂—, —CONHCH₂CH₂—), 6.30 (1H, brs, —CONH—)

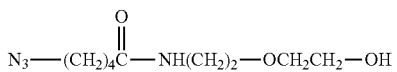

(40)

Example 16

A compound of formula (41) was obtained by allowing to react the compound of formula (40) with methanesulfonyl chloride in toluene in the presence of triethylamine in a manner similar to Example 6.

¹H-NMR (CDCl₃, internal standard TMS); δ (ppm): 1.60-1.74 (4H, m, —CH₂CH₂CH₂CH₂N₃), 2.18 (2H, t, —CH₂CH₂CH₂CH₂N₃), 3.08 (3H, s, —OSO₂CH₃), 3.29 (2H, t, —CH₂CH₂CH₂CH₂N₃), 3.40-3.85 (6H, m, —CONHCH₂CH₂—OCH₂—), 4.37-4.39 (2H, m, —CH₂OSO₂CH₃), 6.30 (1H, brs, —CH₂CONH—)

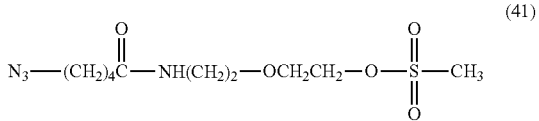

(41)

Example 17

A compound of formula (42) was obtained using 3-fluoro-4-hydroxybenzaldehyde and the compound of formula (41) in the same manner as in Examples 1 to 5 and 7.

$^1$H-NMR (CDCl$_3$, internal standard TMS); δ (ppm): 1.38-1.80 (10H, m, >CHC$\underline{H}_2$C$\underline{H}_2$C$\underline{H}_2$—, —CH$_2$CH$_2$C$\underline{H}_2$CH$_2$N$_3$), 2.18 (2H, t, —C$\underline{H}_2$CH$_2$CH$_2$CH$_2$N$_3$), 3.28-4.23 (15H, m, —OC$\underline{H}_2$C$\underline{H}_2$, —CH$_2$CH$_2$CH$_2$C$\underline{H}_2$N$_3$, —CH$_2$CONHC$\underline{H}_2$C$\underline{H}_2$—, —OC$\underline{H}_2$C$\underline{H}$, —C$\underline{H}_2$-phthalimide), 5.70 (0.6H, s, >C$\underline{H}$—), 5.82 (0.4H, s, >C$\underline{H}$—), 6.30 (1H, brs, —CH$_2$CON$\underline{H}$—), 6.95-7.21 (3H, m, arom.$\underline{H}$), 7.70-7.86 (4H, m, -phthalimide)

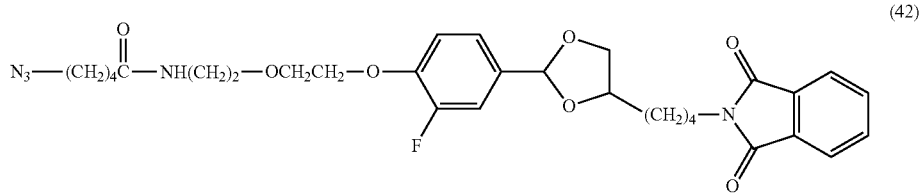

(42)

Example 18

A compound of formula (43) was obtained by deprotecting the phthalimide group from the compound of formula (42) in the same manner as in Example 8.

$^1$H-NMR (CDCl$_3$, internal standard TMS); δ (ppm): 1.38-1.80 (10H, m, >CHC$\underline{H}_2$C$\underline{H}_2$C$\underline{H}_2$—, —CH$_2$C$\underline{H}_2$CH$_2$CH$_2$N$_3$), 2.18 (2H, t, —C$\underline{H}_2$CH$_2$CH$_2$CH$_2$N$_3$), 2.77 (2H, t, —C$\underline{H}_2$—NH$_2$), 3.28-4.23 (13H, m, —OC$\underline{H}_2$C$\underline{H}_2$—, —CH$_2$CH$_2$CH$_2$C$\underline{H}_2$N$_3$, —CH$_2$CONHC$\underline{H}_2$C$\underline{H}_2$—, —OC$\underline{H}_2$C$\underline{H}$<), 5.70 (0.6H, s, >C$\underline{H}$—), 5.82 (0.4H, s, >C$\underline{H}$—), 6.30 (1H, brs, —CH$_2$CON$\underline{H}$—), 6.96 (1H, brs, ICH$_2$CON$\underline{H}$CH$_2$—), 6.95-7.21 (3H, m, arom.$\underline{H}$)

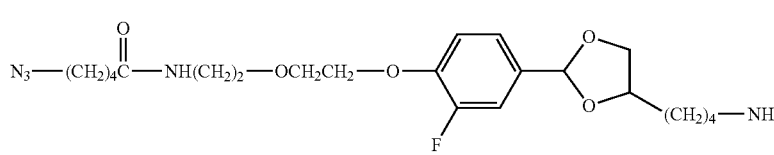

(43)

The hydrolysis test of the cyclic benzylidene acetal linker and synthesis of the polyethylene glycol derivative having the cyclic benzylidene acetal linker used in the hydrolysis test are described below.

In gel permeation chromatography (GPC) analysis, there were used SHODEX GPC SYSTEM-11 as a GPC system, SHODEX RIX8 as a differential refractometer which was a detector, and three columns, i.e., SHODEX KF801L, KF803L and KF804L (φ 8 mm×300 mm) connected in series as GPC columns, and the temperature of the column oven was set to 40° C. The measurement was performed using tetrahydrofuran as an eluent, at the flow rate of 1 ml/minute, at the sample concentration of 0.1% by weight, and in the injection volume of 0.1 ml. The calibration curves prepared by using ethylene glycol, diethylene glycol and triethylene glycol produced by Kanto Chemical Co., Ltd. and Polymer Standards for GPC of polyethylene glycol or polyethylene oxide having a molecular weight of 600 to 70,000 produced by Polymer Laboratory Co., Ltd. were used. For analysis of data, BORWIN GPC calculation program was used. Mn represents a number average molecular weight, Mw represents a weight average molecular weight, and a molecular weight distribution is indicated as a calculated value of Mw/Mn.

A deuterated water buffer of MES (2-morpholinoethanesulfonic acid) having pD of 5.5 and a deuterated water buffer of HEPES (2-[4-(Hydroxyethyl)-1-piperazinyl]ethanesulfonic acid) having pD of 7.4 for use in hydrolysis test were prepared by adding a 0.1M sodium hydroxide deuterated water solution to a 0.1M MES deuterated water solution and a 0.1M HEPES deuterated water solution, respectively, based on the relational equation shown below described in "Glasoe, P. K.; Long, F. A. J. Phys. Chem. 1960, 64, 188-190".

pD=Measured value by pH meter+0.40

A hydrolysis ratio was evaluated by $^1$H-NMR and calculated according to the calculation equation shown below by taking an integrated value of the hydrogen of the acetal group and an integral value of the hydrogen of the aldehyde group to be formed by hydrolysis as $I^1$ and $I^2$, respectively.

Hydrolysis ratio (%)=$[I^2/(I^1+I^2)]\times 100$

Example 19

[ka 54]

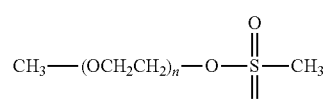

(44)

n = about 113

Into a 100 mL three-necked flask equipped with a thermometer, a nitrogen inlet tube, a stirrer and a condenser tube were charged the compound of formula (44) (5.00 g, 1.00 mmol), the compound of formula (27) (551 mg, 1.50 mmol), potassium carbonate (691 mg, 5.00 mmol) and acetonitrile (25 g), and the reaction was performed at 80° C. for 4 hours. After distilled off the solvent under a reduce pressure, the residue was dissolved in ethyl acetate (100 g) and the solution was filtered. Crystallization was performed by adding hexane (100 g), and after filtration, the crystals were dried under a reduced pressure to obtain a compound of formula (45).

$^1$H-NMR (CDCl$_3$, internal standard TMS); δ (ppm): 1.40-1.81 (6H, m, >CHC$\underline{H}_2$C$\underline{H}_2$C$\underline{H}_2$—), 3.38 (3H, s, C$\underline{H}_3$O—), 3.52-4.25 (455H, m, —(OC$\underline{H}_2$C$\underline{H}_2$)$_n$—, —OC$\underline{H}_2$CH<, —C$\underline{H}_2$- phthalimide), 5.72 (0.6H, s, >C$\underline{H}$—), 5.84 (0.4H, s, >C$\underline{H}$—), 6.89-6.91 (2H, m, arom.$\underline{H}$), 7.35-7.39 (2H, m, arom.$\underline{H}$), 7.70-7.86 (4H, m, -phthalimide)

GPC analysis; number average molecular weight (Mn): 5462, weight average molecular weight (Mw): 5582, polydispersity (Mw/Mn): 1.022

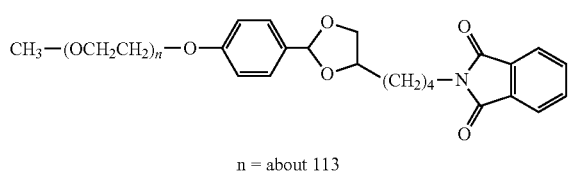

(45)

n = about 113

Example 20

A compound of formula (46) was obtained in the same manner as in Examples 1 to 5 and 19 using 3-fluoro-4-hydroxybenzaldehyde.

$^1$H-NMR (CDCl$_3$, internal standard TMS); δ (ppm): 1.38-1.80 (6H, m, >CHC$\underline{H}_2$C$\underline{H}_2$C$\underline{H}_2$—), 3.38 (3H, s, C$\underline{H}_3$O—), 3.52-4.23 (455H, m, —(OC$\underline{H}_2$C$\underline{H}_2$)$_n$—, —OC$\underline{H}_2$CH<, —C$\underline{H}_2$- phthalimide), 5.70 (0.6H, s, >C$\underline{H}$—), 5.82 (0.4H, s, >C$\underline{H}$—), 6.95-7.21 (3H, m, arom.$\underline{H}$), 7.70-7.86 (4H, m, -phthalimide)

GPC analysis; number average molecular weight (Mn): 5485, weight average molecular weight (Mw): 5606, polydispersity (Mw/Mn): 1.022

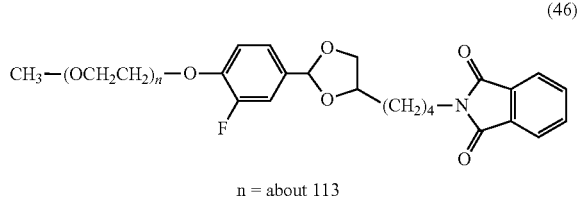

(46)

n = about 113

Example 21

A compound of formula (47) was obtained in the same manner as in Examples 1 to 5 and 19 using 2-bromo-5-hydroxybenzaldehyde.

$^1$H-NMR (CDCl$_3$, internal standard TMS); δ (ppm): 1.38-1.80 (6H, m, >CHC$\underline{H}_2$C$\underline{H}_2$C$\underline{H}_2$—), 3.38 (3H, s, C$\underline{H}_3$O—), 3.52-4.23 (455H, m, —(OC$\underline{H}_2$C$\underline{H}_2$)$_n$—, —OC$\underline{H}_2$CH<, —C$\underline{H}_2$- phthalimide), 5.70 (0.6H, s, >C$\underline{H}$—), 5.82 (0.4H, s, >C$\underline{H}$—), 6.95-7.21 (3H, m, arom.$\underline{H}$), 7.70-7.86 (4H, m, -phthalimide)

GPC analysis; number average molecular weight (Mn): 5548, weight average molecular weight (Mw): 5670, polydispersity (Mw/Mn): 1.022

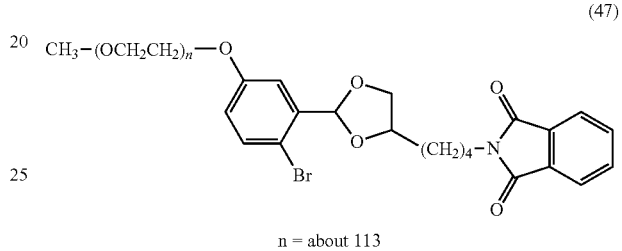

(47)

n = about 113

Example 22

A compound of formula (48) was obtained in the same manner as in Examples 13 and 19 using the compound of formula (36) and 3-fluoro-4-hydroxybenzaldehyde.

$^1$H-NMR (CDCl$_3$, internal standard TMS); δ (ppm): 1.89 (3H, m, —C$\underline{H}_2$C$\underline{H}_2$-phthalimide), 3.19 (1H, m, —OCH$_2$C$\underline{H}$<), 3.38 (3H, s, C$\underline{H}_3$O—), 3.52-4.41 (456H, m, —(OC$\underline{H}_2$C$\underline{H}_2$)$_n$—, —OC$\underline{H}_2$CH<, —C$\underline{H}_2$C$\underline{H}_2$C$\underline{H}_2$-phthalimide), 5.34 (0.8H, s, >C$\underline{H}$—), 5.42 (0.2H, s, >C$\underline{H}$—), 6.95-7.25 (3H, m, arom.$\underline{H}$), 7.70-7.86 (4H, m, -phthalimide)

GPC analysis; number average molecular weight (Mn): 5498, weight average molecular weight (Mw): 5619, polydispersity (Mw/Mn): 1.022

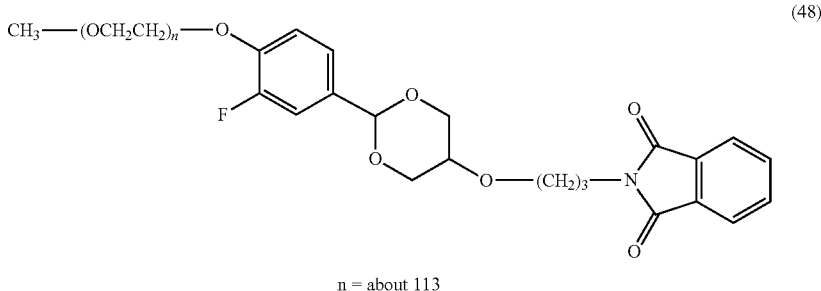

(48)

n = about 113

Example 23

A compound of formula (49) was obtained in the same manner as in Examples 13 to 19 using the compound of formula (36) and 2-bromo-5-hydroxybenzaldehyde.

$^1$H-NMR (CDCl$_3$, internal standard T$_{MS}$); δ (ppm): 1.89 (3H, m, —CH$_2$CH$_2$-phthalimide), 3.19 (1H, m, —OCH$_2$CH<), 3.38 (3H, s, CH$_3$O—), 3.52-4.41 (456H, m, —(OCH$_2$CH$_2$)$_n$—, —OCH$_2$CH<, —CH$_2$CH$_2$CH$_2$-phthalimide), 5.61 (0.8H, s, >CH—), 5.68 (0.2H, s, >CH—), 6.78-7.40 (3H, m, arom.H), 7.70-7.86 (4H, m, -phthalimide)

GPC analysis; number average molecular weight (Mn): 5564, weight average molecular weight (Mw): 5686, polydispersity (Mw/Mn): 1.022

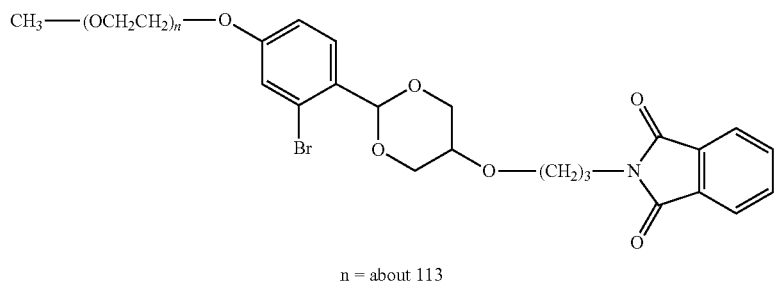

(49)

n = about 113

Example 24

Each of the compounds of formula (45), formula (46), formula (47), formula (48) and formula (49) (20 mg) was dissolved in MES deuterated water buffer having pD of 5.5 (1 mL) or HEPES deuterated water buffer having pD of 7.4 (1 mL) and the solutions were allowed to stand in a thermostatic bath at 37° C. FIG. 1 and FIG. 2 show the measurement results of hydrolysis ratio at pD 5.5 and pD 7.4, respectively.

As shown in FIG. 1, the hydrolysis ratio half-lives (t$_{1/2}$) of the compounds of formula (45), formula (46), formula (47), formula (48) and formula (49) at pD 5.5 and 37° C. were 2 hours, 12 hours, 30 days, 24 hours and 6 months, respectively. Moreover, at pD 7.4 and 37° C. the hydrolysis ratio half-lives (t$_{1/2}$) of the compounds of formula (45) and formula (46) were 65 hours and 18 days, respectively. Although the hydrolysis of approximately 17% was observed for the compound of formula (48) at 18 days, no hydrolysis was observed for the compounds of formula (47) and formula (49) even after 18 days.

Example 25

Chimeric monoclonal antibody AC10 which is IgG1 to CD30 antigen (Wahl, A. F. et al. Cancer Res. 2002, 62, 3736-3742) was prepared according to the literature (Doronina, S. O. et al. Nat. Biotechnot. 2003, 21, 778-784).

Example 26

A doxorubicin derivative having a cyclic benzylidene acetal linker bound was obtained by reacting N-hydroxysuccinimidyl carbonate group of the Compound of formula (34) with doxorubicin hydrochloride (Sigma-Aldrich) in the presence of diisopropylethylamine.

Example 27

AC10 (5 mg/mL) in PBS buffer of pH 8.0 containing 50 mM of sodium borate was treated with dithiothreitol (DTT) (10 mM) at 37° C. for 30 minutes. After gel filtration (Sephadex G-25, PBS containing 1 mM of DTPA), the thiol measurement using 5,5'-dithiobis(2-nitrobenzoic acid) was performed to confirm the presence of approximately eight thiols per antibody. To the reduced AC10 was added the doxorubicin derivative described above (1.2 molar equivalent/thiol) dissolved in ice cooled DMSO (20 mM) at 4° C. After one hour, the reaction was terminated with excess cysteine, the antibody-drug conjugate was concentrated by centrifugal ultrafiltration, gel filtration (Sephadex G-25, PBS) and aseptic filtration. The drug retention rate of the antibody-drug conjugate was determined by measuring absorbances at 280 nm and 490 nm (doxorubicin absorbance) and it was found that the antibody-drug conjugate had 6.8 drugs/antibody.

Example 28

To AC10 (20 mg/mL) in PBS buffer of pH 6.5 (50 mM of potassium phosphate/50 mM of sodium chloride/2 mM of EDTA) was added 7.5 molar equivalent of dibenzocyclooctyne N-hydroxysuccinimidylcarbonate (Sigma-Aldrich) dissolved in ice cooled DMSO (20 mM), and after stirring the mixture for one hour, the compound of formula (43) was added thereto, followed by further stirring for 2 hours. Subsequently, p-nitrophenylcarbonate derivative of (S)-(+)-camptothecin synthesized by the method described in the literature (Angew. Chem. Int. Ed. Engl. 2003, 42, 327-332) was dissolved in ice cooled DMSO (20 mM) and added to the solution described above, followed by further stirring for 2 hours. The reaction mixture was subjected to centrifugal ultrafiltration, gel filtration (Sephadex G-25, PBS) and aseptic filtration to concentrate the antibody-drug conjugate. The drug retention rate of the antibody-drug conjugate was determined by measuring absorbances at 280 nm and 351 nm (camptothecin absorbance) and it was found that the antibody-drug conjugate had 5.2 drugs/antibody.

While the invention has been described in detail and with reference to specific embodiments thereof, it will be apparent to those skilled in the art that various changes and modifications can be made therein without departing from the spirit and scope of the invention.

This application is based on a Japanese patent application filed on Oct. 24, 2014 (Japanese Patent Application No. 2014-217466), and the whole contents thereof are incorporated herein by reference. Also, all the references cited herein are incorporated as a whole.

The invention claimed is:

1. An antibody-drug conjugate having a cyclic benzylidene acetal linker represented by formula (1) or formula (2):

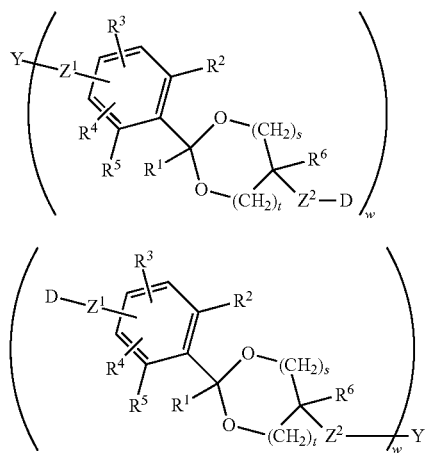

wherein, in the formula (1) and the formula (2), Y is an antibody; D is a drug; $R^1$ and $R^6$ are each independently a hydrogen atom or a hydrocarbon group; $R^2$, $R^3$, $R^4$ and $R^5$ are each independently an electron-withdrawing or electron-donating substituent or a hydrogen atom; s is 1 or 2, t is 0 or 1, and s+t is 1 or 2; w is an integer of 1 to 20; and each of $Z^1$ and $Z^2$ is a divalent spacer composed of a structural unit independently selected from an ether group, an ester group, a carbonate group, a urethane group, an amide group, a thioether group, a disulfide group, a 1H-1,2,3-triazole-1,4-diyl group, a secondary amino group, an aliphatic hydrocarbon group containing any of these groups, or an aliphatic hydrocarbon group; or each of $Z^1$ and $Z^2$ is a divalent spacer composed of two identical structural units selected from an ether group, an ester group, a carbonate group, a urethane group, an amide group, a thioether group, a disulfide group, a 1H-1,2,3-triazole-1,4-diyl group, a secondary amino group or an aliphatic hydrocarbon group containing any of these groups.

2. The antibody-drug conjugate as claimed in claim 1, wherein $Z^1$ and $Z^2$ are each independently selected from the group consisting of structure (z1), structure (z2), structure (z3), structure (z4), structure (z5), structure (z6), structure (z7), structure (z8), structure (z9), and structure (z10):

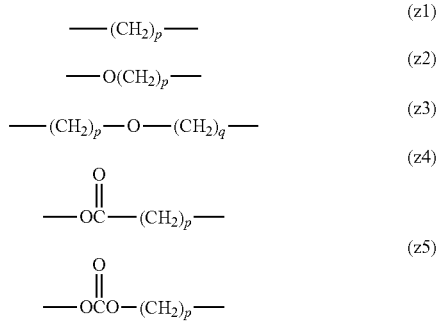

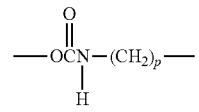

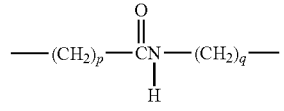

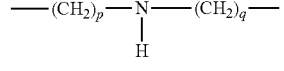

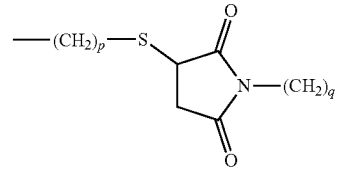

wherein p and q are each independently an integer of 1 to 12.

3. The antibody-drug conjugate as claimed in claim 1, wherein s is 1 and t is 0, $R^2$ and $R^5$ are each a hydrogen atom, and a sum ($\Sigma\sigma$) of substituent constants ($\sigma$) in $R^3$, $R^4$ and Y—$Z^1$ in the formula (1) or in $R^3$, $R^4$ and D-$Z^1$ in the formula (2) satisfies $-0.30 \leq \Sigma\sigma \leq 1.05$.

4. The antibody-drug conjugate as claimed in claim 1, wherein s is 1 and t is 0, at least one of $R^2$ and $R^5$ is the substituent, and a sum ($\Sigma\sigma$) of substituent constants ($\sigma$) in $R^3$, $R^4$ and Y—$Z^1$ in the formula (1) or in $R^3$, $R^4$ and D-$Z^1$ in the formula (2) satisfies $-1.71 \leq \Sigma\sigma \leq 0.88$.

5. The antibody-drug conjugate as claimed in claim 1, wherein s is 1 and t is 1, or s is 2 and t is 0, $R^2$ and $R^5$ are each a hydrogen atom, and a sum ($\Sigma\sigma$) of substituent constants ($\sigma$) in $R^3$, $R^4$ and Y—$Z^1$ in the formula (1) or in $R^3$, $R^4$ and D-$Z^1$ in the formula (2) satisfies $-0.19 \leq \Sigma\sigma \leq 0.57$.

6. The antibody-drug conjugate as claimed in claim 1, wherein s is 1 and t is 1, or s is 2 and t is 0, at least one of $R^2$ and $R^5$ is the substituent, and a sum ($\Sigma\sigma$) of substituent constants ($\sigma$) in $R^3$, $R^4$ and Y—$Z^1$ in the formula (1) or in $R^3$, $R^4$ and D-$Z^1$ in the formula (2) satisfies $-0.98 \leq \Sigma\sigma \leq 0.48$.

7. The antibody-drug conjugate as claimed in claim 1, wherein the antibody is a monoclonal antibody, a single chain monoclonal antibody, a bispecific antibody or a monoclonal antibody fragment that binds to a target cell.

8. The antibody-drug conjugate as claimed in claim 1, wherein the antibody is a resurfaced monoclonal antibody, a resurfaced single chain monoclonal antibody or a resurfaced monoclonal antibody fragment that binds to a target cell.

9. The antibody-drug conjugate as claimed in claim 1, wherein the antibody is a human monoclonal antibody, a humanized monoclonal antibody, a humanized single chain monoclonal antibody or a humanized monoclonal antibody fragment that binds to a target cell.

10. The antibody-drug conjugate as claimed in claim 7, wherein the antibody is a chimeric antibody, a chimeric antibody fragment, a domain antibody or a domain antibody fragment.

11. The antibody-drug conjugate as claimed in claim 1, wherein the drug is a chemotherapeutic drug.

* * * * *